(12) United States Patent
Binch et al.

(10) Patent No.: US 8,598,205 B2
(45) Date of Patent: *Dec. 3, 2013

(54) MODULATORS OF CYSTIC FIBROSIS TRANSMEMBRANE CONDUCTANCE REGULATOR

(75) Inventors: Hayley Binch, Encinitas, CA (US); Lev T. D. Fanning, San Marcos, CA (US); Dennis Hurley, San Marcos, CA (US); Urvi Sheth, San Diego, CA (US); Alina Silina, San Diego, CA (US); Xiaoqing Yang, San Diego, CA (US); Martyn Botfield, Concord, MA (US); Peter D. J. Grootenhuis, San Diego, CA (US); Fredrick Van Goor, San Diego, CA (US); Mehdi Michel Djamel Numa, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/439,379

(22) Filed: Apr. 4, 2012

(65) Prior Publication Data

US 2012/0208841 A1 Aug. 16, 2012

Related U.S. Application Data

(63) Continuation of application No. 12/605,053, filed on Oct. 23, 2009.

(60) Provisional application No. 61/107,830, filed on Oct. 23, 2008.

(51) Int. Cl.
C07D 215/38 (2006.01)
A61K 31/04 (2006.01)

(52) U.S. Cl.
USPC ........................... 514/312; 546/159

(58) Field of Classification Search
USPC ........................... 546/159; 514/312
See application file for complete search history.

(56) References Cited

U.S. PATENT DOCUMENTS

| | | | |
|---|---|---|---|
| 4,450,167 A | 5/1984 | Le Martret et al. | |
| 4,908,366 A | 3/1990 | Schriewer et al. | |
| 4,956,465 A | 9/1990 | Schriewer et al. | |
| 6,506,792 B1 | 1/2003 | Reed et al. | |
| 7,407,976 B2 | 8/2008 | Miller et al. | |
| 7,495,103 B2 * | 2/2009 | Hadida-Ruah et al. | 546/156 |
| 7,553,855 B2 | 6/2009 | Young et al. | |
| 7,598,412 B2 | 10/2009 | Hadida Ruah et al. | |
| 7,645,789 B2 | 1/2010 | Hadida Ruah et al. | |
| 7,659,268 B2 | 2/2010 | Hadida Ruah et al. | |
| 7,671,221 B2 | 3/2010 | Hadida Ruah et al. | |
| 7,691,902 B2 | 4/2010 | Hadida Ruah et al. | |
| 7,741,321 B2 | 6/2010 | Hadida Ruah et al. | |
| 7,754,739 B2 | 7/2010 | Hadida Ruah et al. | |
| 7,776,905 B2 | 8/2010 | Hadida Ruah et al. | |
| 7,846,951 B2 | 12/2010 | Miller et al. | |
| 7,956,052 B2 | 6/2011 | Hadida Ruah et al. | |
| 7,973,038 B2 | 7/2011 | Hadida Ruah et al. | |
| 7,973,169 B2 | 7/2011 | Hadida Ruah et al. | |
| 7,977,322 B2 | 7/2011 | Hadida Ruah et al. | |
| 7,999,113 B2 | 8/2011 | Hadida Ruah et al. | |
| 8,012,999 B2 | 9/2011 | Hadida Ruah et al. | |
| 8,039,491 B2 | 10/2011 | Hadida Ruah et al. | |
| 8,076,357 B2 | 12/2011 | Young et al. | |
| 8,101,767 B2 * | 1/2012 | Ruah et al. | 546/159 |
| 8,124,781 B2 | 2/2012 | Siesel | |
| 8,163,772 B2 | 4/2012 | Demattei et al. | |
| 8,188,283 B2 | 5/2012 | Binch et al. | |
| 8,227,615 B2 | 7/2012 | Hadida Ruah et al. | |
| 8,232,302 B2 | 7/2012 | Miller et al. | |
| 2005/0059687 A1 | 3/2005 | Makings et al. | |
| 2005/0113423 A1 | 5/2005 | Van Goor et al. | |
| 2006/0025327 A1 | 2/2006 | Sanchez et al. | |
| 2006/0052358 A1 | 3/2006 | Ruah et al. | |
| 2006/0156485 A1 | 7/2006 | Lim | |
| 2007/0105833 A1 | 5/2007 | Ruah et al. | |
| 2007/0238775 A1 | 10/2007 | Ruah et al. | |
| 2007/0264196 A1 | 11/2007 | Ruah et al. | |
| 2008/0071095 A1 | 3/2008 | Ruah et al. | |
| 2008/0293739 A1 | 11/2008 | Trede | |
| 2008/0306062 A1 | 12/2008 | Ruah et al. | |
| 2009/0105272 A1 | 4/2009 | Grootenhuis et al. | |
| 2009/0143381 A1 | 6/2009 | Ruah et al. | |
| 2009/0170905 A1 | 7/2009 | Keshavarz-Shokri et al. | |
| 2009/0176839 A1 | 7/2009 | Keshavarz-Shokri et al. | |
| 2009/0221597 A1 | 9/2009 | Ruah et al. | |
| 2009/0246820 A1 | 10/2009 | Singh et al. | |
| 2009/0253736 A1 | 10/2009 | Ruah et al. | |
| 2009/0298876 A1 | 12/2009 | Hadida Ruah et al. | |
| 2010/0036130 A1 | 2/2010 | Siesel | |
| 2010/0074949 A1 | 3/2010 | Rowe et al. | |
| 2010/0087490 A1 | 4/2010 | Young | |
| 2010/0113508 A1 * | 5/2010 | Binch et al. | 514/304 |

(Continued)

FOREIGN PATENT DOCUMENTS

EP 0059698 A1 9/1982
EP 0324521 A2 7/1989

(Continued)

OTHER PUBLICATIONS

ISR of PCT/US2009/061882, dated Jul. 15, 2010.
Kleinerman, Ellen, "Breakthrough Drug Announced for Cystic Fibrosis Treatment," [online], Nov. 2, 2011 [Retrieved on May 15, 2012]. Retrieved from the Internet<http://www.cleveland.com/healthfit/index.ssf/2011/11/ breakthrough_drug_announced_fo.html>, pp. 1-6.

*Primary Examiner* — D M Seaman
(74) *Attorney, Agent, or Firm* — Honigman Miller Schwartz and Cohn LLP; Christopher C. Forbes; Jonathan P. O'Brien

(57) ABSTRACT

The present invention relates to modulators of cystic fibrosis transmembrane conductance regulator ("CFTR"), compositions thereof, and methods therewith. The present invention also relates to methods of treating diseases using modulators of CFTR.

22 Claims, No Drawings

(56) References Cited

U.S. PATENT DOCUMENTS

| | | |
|---|---|---|
| 2010/0113509 A1 | 5/2010 | Binch et al. |
| 2010/0113555 A1 | 5/2010 | Hadida Ruah et al. |
| 2010/0125090 A1 | 5/2010 | Hadida Ruah et al. |
| 2010/0130547 A1* | 5/2010 | Zhang et al. ............... 514/312 |
| 2010/0144798 A1 | 6/2010 | Van Goor et al. |
| 2010/0168094 A1 | 7/2010 | Binch et al. |
| 2010/0168158 A1 | 7/2010 | Binch et al. |
| 2010/0184739 A1 | 7/2010 | Sheth et al. |
| 2010/0249113 A1 | 9/2010 | Hadida Ruah et al. |
| 2010/0249180 A1 | 9/2010 | Gallardo-Godoy |
| 2010/0256184 A1 | 10/2010 | Rowe et al. |
| 2010/0267768 A1 | 10/2010 | Demattei et al. |
| 2010/0331344 A1 | 12/2010 | Hadida Ruah et al. |
| 2011/0008259 A1 | 1/2011 | Binch et al. |
| 2011/0060024 A1 | 3/2011 | Hadida Ruah et al. |
| 2011/0064811 A1 | 3/2011 | Hurter et al. |
| 2011/0065928 A1 | 3/2011 | Ambhaikar et al. |
| 2011/0071206 A1 | 3/2011 | Ruah et al. |
| 2011/0098311 A1 | 4/2011 | Van Goor et al. |
| 2011/0123449 A1* | 5/2011 | Zhang et al. ............... 424/9.1 |
| 2011/0124869 A1 | 5/2011 | Ambhaikar et al. |
| 2011/0172229 A1 | 7/2011 | Hadida Ruah et al. |
| 2011/0177999 A1 | 7/2011 | Singh et al. |
| 2011/0257223 A1* | 10/2011 | Goor et al. ............... 514/304 |
| 2011/0263654 A1 | 10/2011 | Keshavarz-Shokri et al. |
| 2011/0288121 A1 | 11/2011 | Sun et al. |
| 2011/0288122 A1 | 11/2011 | Van Goor et al. |
| 2011/0306637 A1 | 12/2011 | Hadida Ruah et al. |
| 2011/0312958 A1 | 12/2011 | Hadida Ruah et al. |
| 2012/0004216 A1 | 1/2012 | Hadida Ruah et al. |
| 2012/0010257 A1 | 1/2012 | Hadida Ruah et al. |
| 2012/0015999 A1 | 1/2012 | Alargova et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | Demattei et al. |
| 2012/0122922 A1 | 5/2012 | Young et al. |
| 2012/0165372 A1 | 6/2012 | Demattei et al. |
| 2012/0184583 A1 | 7/2012 | Van Goor et al. |
| 2012/0190856 A1 | 7/2012 | Siesel |
| 2013/0035327 A1* | 2/2013 | Hadida-Ruah et al. .. 514/213.01 |

FOREIGN PATENT DOCUMENTS

| | | |
|---|---|---|
| FR | 2537140 A1 | 6/1984 |
| JP | 2009051827 A | 3/2009 |
| JP | 2009051828 A | 3/2009 |
| WO | 9704779 A1 | 2/1997 |
| WO | 9748694 A1 | 12/1997 |
| WO | 0012623 A2 | 3/2000 |
| WO | 0042026 A1 | 7/2000 |
| WO | 0073283 A1 | 12/2000 |
| WO | 0134596 A2 | 5/2001 |
| WO | 0206264 A1 | 1/2002 |
| WO | 0207516 A2 | 1/2002 |
| WO | 0212189 A1 | 2/2002 |
| WO | 02068417 A2 | 9/2002 |
| WO | 02096424 A1 | 12/2002 |
| WO | 03049702 A2 | 6/2003 |
| WO | 2004014377 A1 | 2/2004 |
| WO | 2004065351 A1 | 8/2004 |
| WO | 2005094805 A1 | 10/2005 |
| WO | 2006002421 A2 | 1/2006 |
| WO | 2007071055 A2 | 6/2007 |
| WO | 2007088999 A1 | 8/2007 |
| WO | 2008031556 A2 | 3/2008 |
| WO | 2008112715 A2 | 9/2008 |
| WO | 2008154221 A2 | 12/2008 |
| WO | 2009010454 A2 | 1/2009 |
| WO | 2009036412 A1 | 3/2009 |
| WO | 2010073078 A2 | 7/2010 |
| WO | 2010127452 A1 | 11/2010 |
| WO | 2011009540 A2 | 1/2011 |
| WO | 2011018170 A2 | 2/2011 |

* cited by examiner

MODULATORS OF CYSTIC FIBROSIS TRANSMEMBRANE CONDUCTANCE REGULATOR

CROSS-REFERENCE TO RELATED APPLICATIONS

The present application is a continuation of U.S. Ser. No. 12/605,053, filed on Oct. 23, 2009, which claims the benefit of priority under 35 U.S.C. §119 to U.S. Provisional Application Ser. No. 61/107,830, filed Oct. 23, 2008 and entitled "MODULATORS OF CYSTIC FIBROSIS TRANSMEMBRANE CONDUCTANCE REGULATOR," the entire contents of which is incorporated herein by reference.

TECHNICAL FIELD OF THE INVENTION

The present invention relates to modulators of cystic fibrosis transmembrane conductance regulator ("CFTR"), compositions thereof, and methods therewith. The present invention also relates to methods of treating diseases using modulators of CFTR.

BACKGROUND OF THE INVENTION

ATP cassette transporters are a family of membrane transporter proteins that regulate the transport of a wide variety of pharmacological agents, potentially toxic drugs, and xenobiotics, as well as anions. They are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 such transporters have been identified and grouped into 7 families based on their sequence identity and function.

One member of the ATP cassette transporters family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, more than 1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia, leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dolmans et al. (1991), Nature Lond. 354: 526-528; Denning et al., supra; Pasyk and Foskett (1995), J. Cell. Biochem. 270: 12347-50). In addition to ΔF508-CFTR, R117H-CFTR and G551D-CFTR, other disease causing mutations in CFTR that result in defective trafficking, synthesis, and/or channel gating, could be up- or down-regulated to alter anion secretion and modify disease progression and/or severity.

Although CFTR transports a variety of molecules in addition to anions, it is clear that this role (the transport of anions, chloride and bicarbonate) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl channels expressed on the basolateral surface of the cell. Secondary active transport of chloride from the luminal side leads to the accumulation of intracellular chloride, which can then passively leave the cell via Cl⁻ ion channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Defective bicarbonate transport due to mutations in CFTR is hypothesized to cause defects in certain secretory functions. See, e.g., "Cystic fibrosis: impaired bicarbonate secretion and mucoviscidosis," Paul M. Quinton, Lancet 2008; 372: 415-417.

Mutations in CFTR that are associated with moderate CFTR dysfunction are also evident in patients with conditions that share certain disease manifestations with CF but do not meet the diagnostic criteria for CF. These include congenital bilateral absence of the vas deferens, idiopathic chronic pancreatitis, chronic bronchitis, and chronic rhinosinusitis. Other diseases in which mutant CFTR is believed to be a risk factor along with modifier genes or environmental factors include primary sclerosing cholangitis, allergic bronchopulmonary aspergillosis, and asthma.

Cigarette smoke, hypoxia, and environmental factors that induce hypoxic signaling have also been demonstrated to impair CFTR function and may contribute to certain forms of respiratory disease, such as chronic bronchitis. Diseases that may be due to defective CFTR function but do not meet the diagnostic criteria for CF are characterized as CFTR-related diseases.

In addition to cystic fibrosis, modulation of CFTR activity may be beneficial for other diseases not directly caused by mutations in CFTR, such as secretory diseases and other protein folding diseases mediated by CFTR. CFTR regulates chloride and bicarbonate flux across the epithelia of many cells to control fluid movement, protein solubilization, mucus viscosity, and enzyme activity. Defects in CFTR can cause blockage of the airway or ducts in many organs, including the liver and pancreas. Potentiators are compounds that enhance the gating activity of CFTR present in the cell membrane. Any disease which involves thickening of the mucus, impaired fluid regulation, impaired mucus clearance, or blocked ducts leading to inflammation and tissue destruction could be a candidate for potentiators.

These include, but are not limited to, chronic obstructive pulmonary disease (COPD), asthma, smoke induced COPD, chronic bronchitis, rhinosinusitis, constipation, dry eye disease, and Sjögren's Syndrome, gastro-esophageal reflux disease, gallstones, rectal prolapse, and inflammatory bowel disease. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. In addition, by preventing ongoing infection and inflammation due to improved airway clearance, CFTR modulators may prevent or slow the parenchymal destruction of the airway that characterizes emphysema and reduce or reverse the increase in mucus secreting cell number and size that underlyses mucus hypersecretion in airway diseases. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and may help to alleviate the associated symptoms. Individuals with cystic fibrosis have recurrent episodes of intestinal obstruction and higher incidences of rectal polapse, gallstones, gastro-esophageal reflux disease, GI malignancies, and inflammatory bowel disease, indicating that CFTR function may play an important role in preventing such diseases.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of CFTR by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome (due to Prp processing defect), infertility pancreatitis, pancreatic insufficiency, osteoporosis, osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, and liver disease.

Other diseases implicated by a mutation in CFTR include male infertility caused by congenital bilateral absence of the vas deferens (CBAVD), mild pulmonary disease, idiopathic pancreatitis, and allergic bronchopulmonary aspergillosis (ABPA). See, "CFTR-opathies: disease phenotypes associated with cystic fibrosis transmembrane regulator gene mutations," Peader G. Noone and Michael R. Knowles, Respir. Res. 2001, 2: 328-332 (incorporated herein by reference).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death. Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients with acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Accordingly, there is a need for potent and selective CFTR potentiators of wild-type and mutant forms of human CFTR. These mutant CFTR forms include, but are not limited to, ΔF508del, G551D, R117H, 2789+5G→A.

There is also a need for modulators of CFTR activity, and compositions thereof, which can be used to modulate the activity of the CFTR in the cell membrane of a mammal.

There is a need for methods of treating diseases caused by mutation in CFTR using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of CFTR activity. The compounds have the general Formula (I):

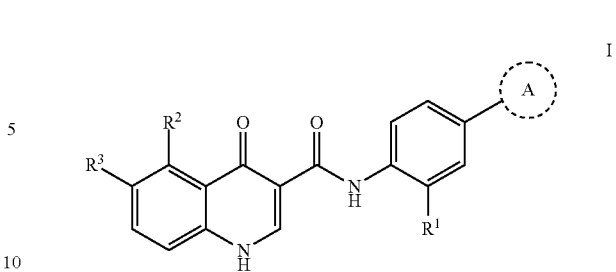

or pharmaceutically acceptable salts thereof, wherein $R^1$, $R^2$, $R^3$ and A are described generally and in classes and subclasses below.

These compounds and pharmaceutically acceptable compositions are useful for treating or lessening the severity of a variety of diseases, disorders, or conditions associated with mutations in CFTR.

DETAILED DESCRIPTION OF THE INVENTION

General Description of Compounds of the Invention

The present invention relates to compounds of Formula (I) useful as modulators of CFTR activity:

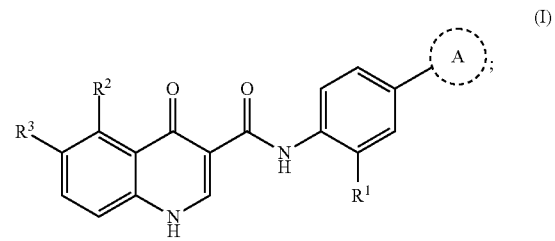

or pharmaceutically acceptable salts thereof, wherein:
ring A is selected from:

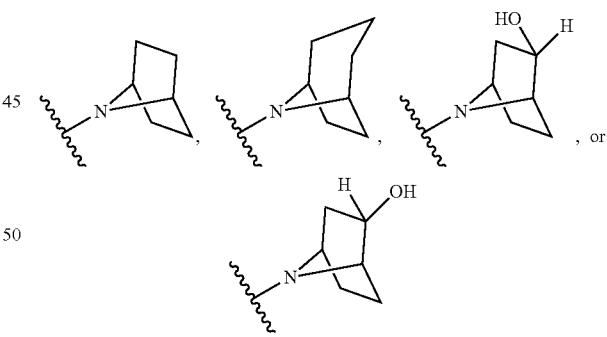

$R^1$ is —$CF_3$, —CN, or —C≡$CCH_2N(CH_3)_2$;
$R^2$ is hydrogen, —$CH_3$, —$CF_3$, —OH, or —$CH_2OH$;
$R^3$ is hydrogen, —$CH_3$, —$OCH_3$, or —CN;
provided that both $R^2$ and $R^3$ are not simultaneously hydrogen.

Compounds and Definitions:

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cftr/, for CFTR mutations).

The term "modulating" as used herein means increasing or decreasing by a measurable amount.

The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "protecting group", as used herein, refers to an agent used to temporarily to block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention; e.g., compounds of Formula (I) may exist as tautomers:

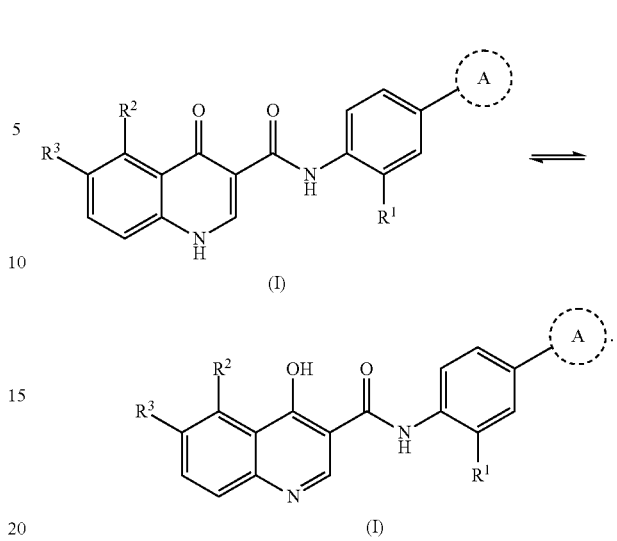

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, particularly compounds that contain deuterium atoms, may exhibit modified metabolic properties.

Description of Exemplary Compounds:

The present invention provides a compound of Formula (I):

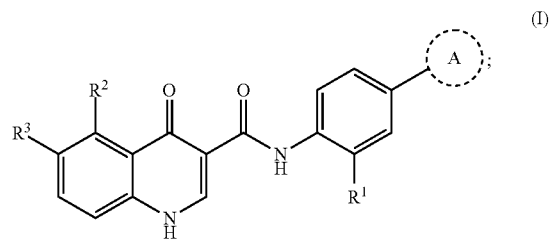

or pharmaceutically acceptable salts thereof, wherein:

ring A is selected from:

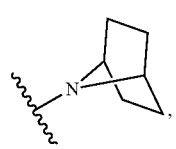

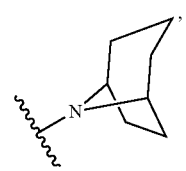

-continued (c)
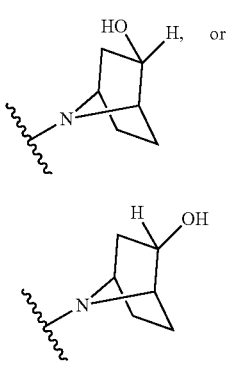
or (d)

R¹ is —CF₃, —CN, or —C≡CCH₂N(CH₃)₂;
R² is hydrogen, —CH₃, —CF₃, —OH, or —CH₂OH;
R³ is hydrogen, —CH₃, —OCH₃, or —CN;
provided that both R² and R³ are not simultaneously hydrogen.

In one embodiment, ring A is (a)
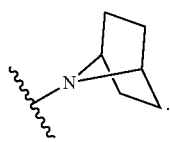

In one embodiment, ring A is (b)
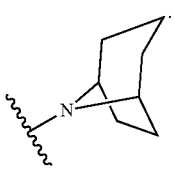 [SMILES: *N1C2CCCC1CC2]

In another embodiment, ring A is

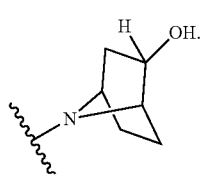

In yet another embodiment, ring A is (d)

In one embodiment, R¹ is —CF₃.
In another embodiment, R¹ is —CN.
In another embodiment, R¹ is —C≡CCH₂N(CH₃)₂.
In one embodiment, R² is —CH₃.
In another embodiment, R² is —CF₃.
In another embodiment, R² is —OH.
In another embodiment, R² is —CH₂OH.
In one embodiment, R³ is —CH₃.
In one embodiment, R³ is —OCH₃.
In another embodiment, R³ is —CN.
In one embodiment, R² is hydrogen; and R³ is —CH₃, —OCH₃, or —CN.
In another embodiment, R² is —CH₃, —CF₃, —OH, or —CH₂OH; and R³ is hydrogen.

In several embodiments of the present invention, ring A is

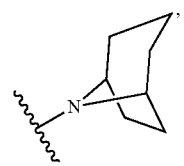

R¹ is —CF₃, R² is hydrogen; and R³ is —CH₃, —OCH₃, or —CN. In other embodiments, R¹ is —CN. In still further embodiments, R¹ is —C≡CCH₂N(CH₃)₂. In one embodiment, R³ is —CH₃. Or, R³ is —OCH₃. Or, R³ is —CN.

In further embodiments of the present invention, ring A is

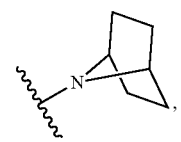 [SMILES: *N1C2CCC1CC2]

R¹ is —CF₃, R² is —CH₃, —CF₃, —OH, or —CH₂OH, and R³ is hydrogen. In other embodiments, R¹ is —CN. In still further embodiments, R¹ is —C≡CCH₂N(CH₃)₂. In one embodiment, R² is —CH₃. Or, R² is —CF₃. Or, R² is —OH. Or, R² is —CH₂OH.

In several embodiments of the present invention, ring A is (c)

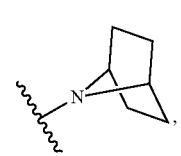

R¹ is —CF₃, R² is hydrogen; and R³ is —CH₃, —OCH₃, or —CN. In other embodiments, R¹ is —CN. In still further embodiments, R¹ is —C≡CCH₂N(CH₃)₂. In one embodiment, R³ is —OCH₃. Or, R³ is —CH₃. Or, R³ is —CN.

In further embodiments of the present invention, ring A is (d)

$R^1$ is —$CF_3$, $R^2$ is —$CH_3$, —$CF_3$, —OH, or —$CH_2OH$, and $R^3$ is hydrogen. In other embodiments, $R^1$ is —CN. In still further embodiments, $R^1$ is —C≡$CCH_2N(CH_3)_2$. In one embodiment, $R^2$ is —$CH_3$. Or, $R^2$ is —$CF_3$. Or, $R^2$ is —OH. Or, $R^2$ is —$CH_2OH$.

In several embodiments of the present invention, ring A is

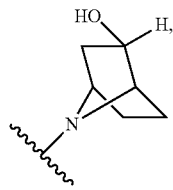

$R^1$ is —$CF_3$, $R^2$ is hydrogen; and $R^3$ is —$CH_3$, —$OCH_3$, or —CN. In other embodiments, $R^1$ is —CN. In still further embodiments, $R^1$ is —C≡$CCH_2N(CH_3)_2$. In one embodiment, $R^3$ is —$CH_3$. Or, $R^3$ is —$OCH_3$. Or, $R^3$ is —CN.

In further embodiments of the present invention, ring A is

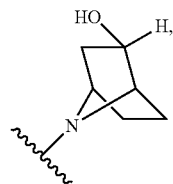

$R^1$ is —$CF_3$, $R^2$ is —$CH_3$, —$CF_3$, —OH, or —$CH_2OH$, and $R^3$ is hydrogen. In other embodiments, $R^1$ is —CN. In still further embodiments, $R^1$ is —C≡$CCH_2N(CH_3)_2$. In one embodiment, $R^2$ is —$CH_3$. Or, $R^2$ is —$CF_3$. Or, $R^2$ is —OH. Or, $R^2$ is —$CH_2OH$.

In several embodiments of the present invention, ring A is

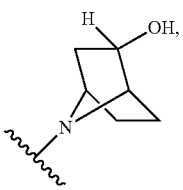 [SMILES: *N1C2CCC1C(O)C2]

$R^1$ is —$CF_3$, $R^2$ is hydrogen; and $R^3$ is —$CH_3$, —$OCH_3$, or —CN. In other embodiments, $R^1$ is —CN. In still further embodiments, $R^1$ is —C≡$CCH_2N(CH_3)_2$. In one embodiment, $R^3$ is —$CH_3$. Or, $R^3$ is —$OCH_3$. Or, $R^3$ is —CN.

In further embodiments of the present invention, ring A is

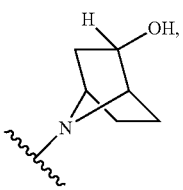 [SMILES: *N1C2CCC1C(O)C2]

$R^1$ is —$CF_3$, $R^2$ is —$CH_3$, —$CF_3$, —OH, or —$CH_2OH$, and $R^3$ is hydrogen. In other embodiments, $R^1$ is —CN. In still further embodiments, $R^1$ is —C≡$CCH_2N(CH_3)_2$. In one embodiment, $R^2$ is —$CH_3$. Or, $R^2$ is —$CF_3$. Or, $R^2$ is —OH. Or, $R^2$ is —$CH_2OH$.

Representative compounds of the present invention are set forth below in Table 1 below.

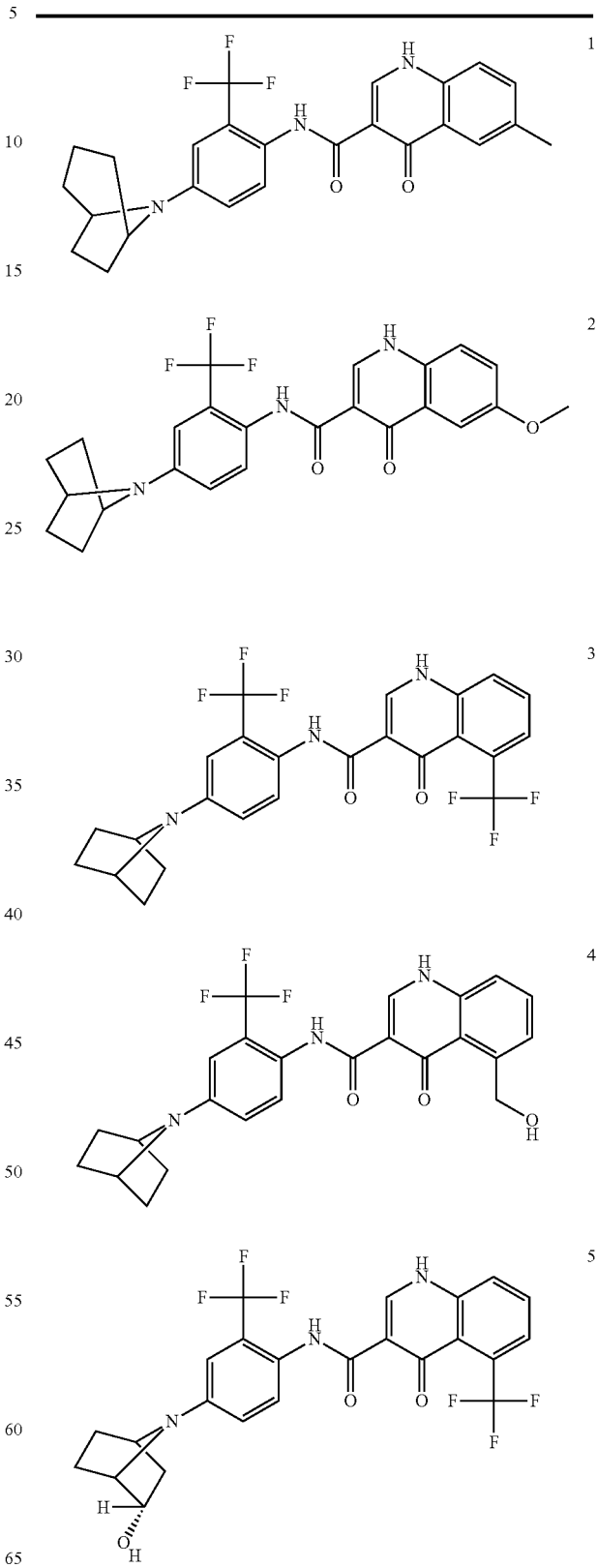

-continued
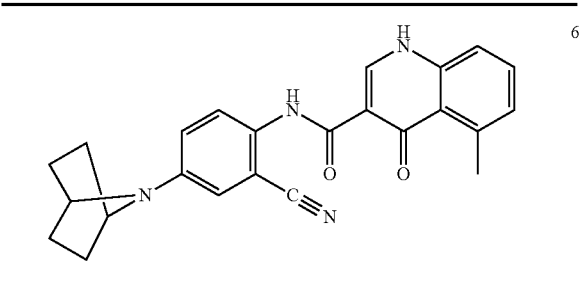
6
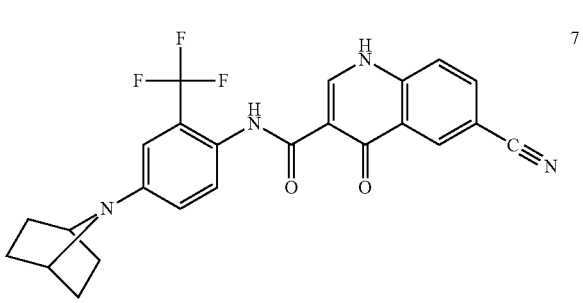
7
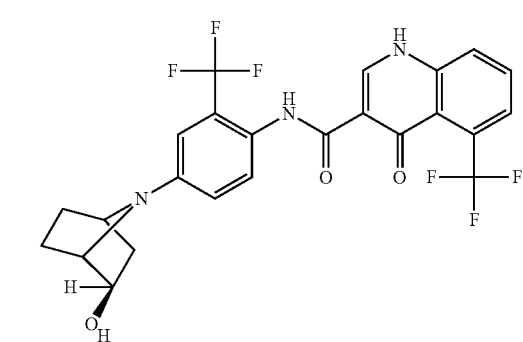
8
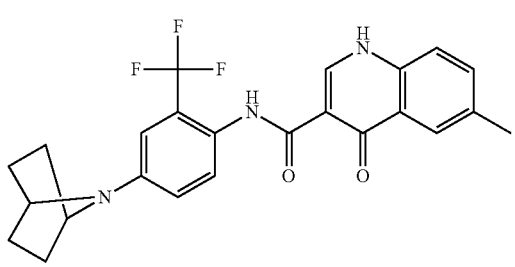 [SMILES: Cc1ccc2[nH]cc(C(=O)Nc3ccc(N4C5CCC4CC5)cc3C(F)(F)F)c(=O)c2c1]
9
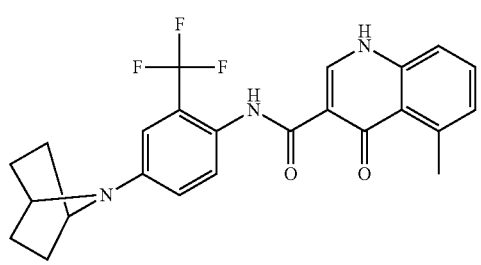 [SMILES: Cc1cccc2[nH]cc(C(=O)Nc3ccc(N4C5CCC4CC5)cc3C(F)(F)F)c(=O)c12]
10
-continued
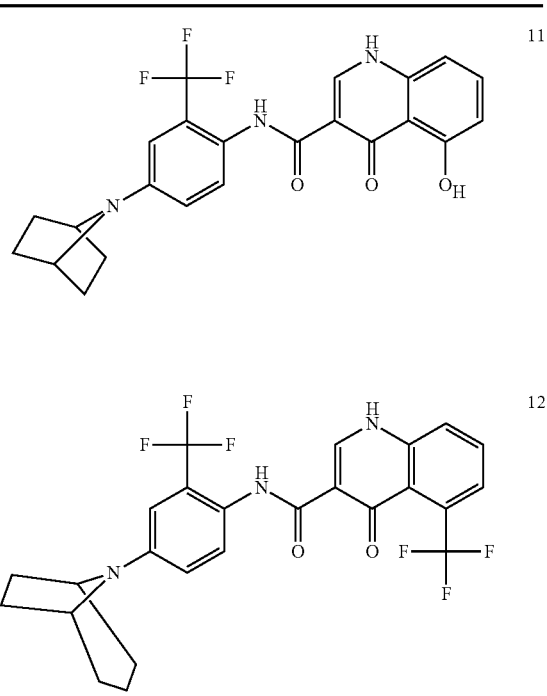
11
12
13
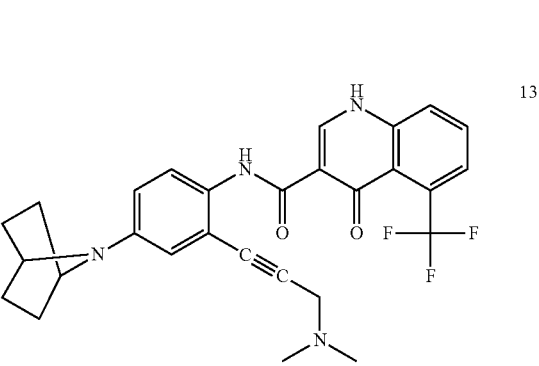
14
General Synthetic Schemes
Compounds of the present invention are readily prepared by methods known in the art, and as depicted in Scheme 1-3.

Scheme 1. Preparation of Compounds of Formula (I).

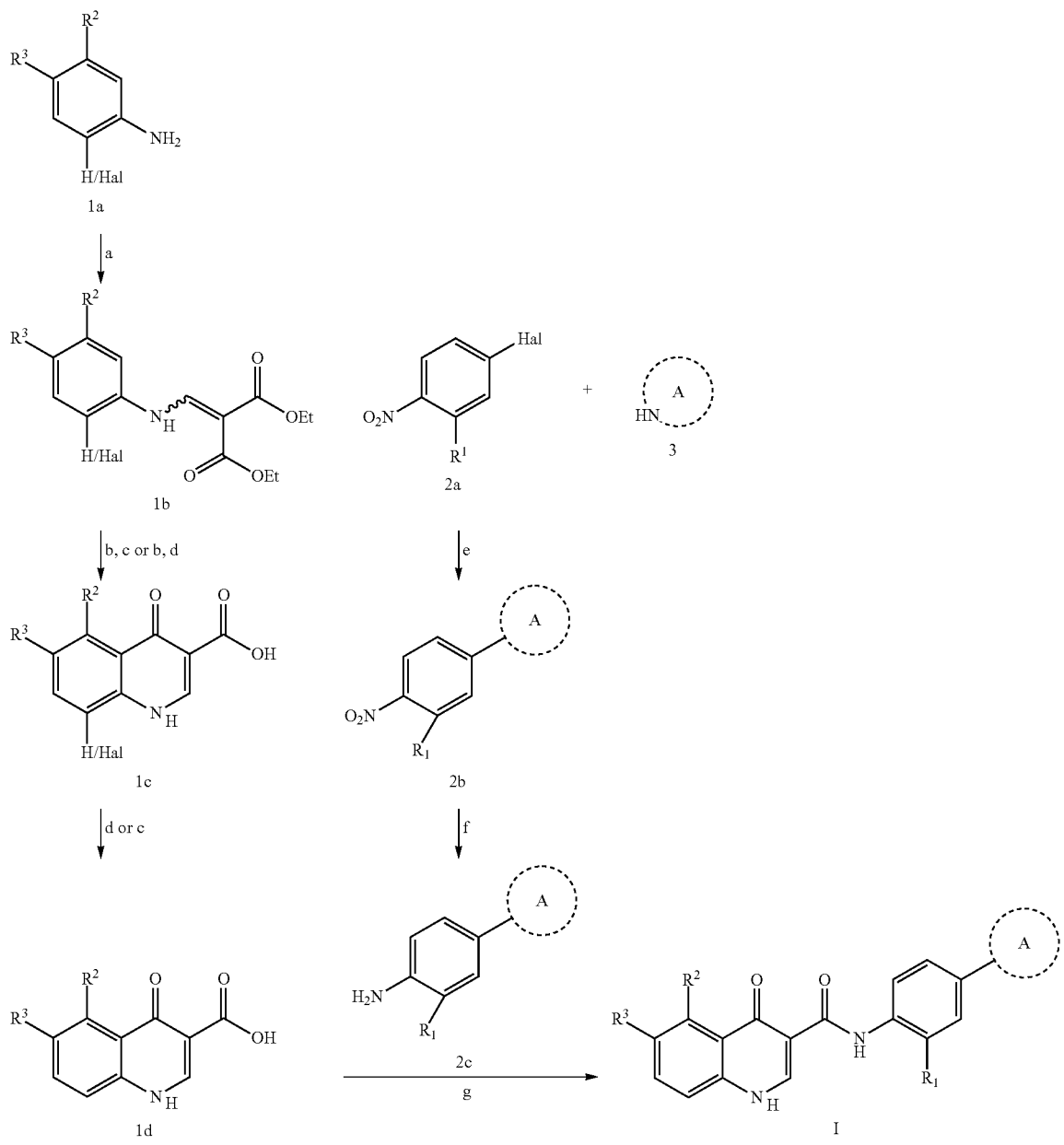

a (CO₂R)₂CH=CH(OR), toluene, heat;
b Dowtherm or diphenyl ether, reflux, N₂ atmosphere;
c Removal of halogen blocking group if present (e.g. —Cl), Pd/C, H₂, EtOH;
d removal of protecting group R by base or acid;
e CH₃CN, Et₃N, heat;
f Pd/C, H₂, EtOH;
g HATU, Et₃N, DMF or propyl phosphonic acid cyclic anhydride (T3P®), pyridine, 2-methyltetrahydrofuran.

Scheme 1 depicts a convergent approach to the preparation of compounds of Formula (I) from substituted benzene derivatives 1a and 2a. In the ultimate transformation, amide formation via coupling of carboxylic acid 1d with amine 2c to give a compound of Formula (I) can be achieved using either O-(7-azabenzotriazol-1-yl)-N,N,N',N'-tetramethyluronium hexafluorophosphate (HATU) and triethylamine in N,N-dimethyl formamide (DMF) or propyl sulfronic acid cyclic anhydride (T3P®) and pyridine in 2-methyltetrahydrofuran. Carboxylic acid 1d is prepared from the corresponding substituted benzene derivative 1a via a sequence commencing with heat-mediated condensation of 1a with an appropriate malonate $(CO_2R)_2CH=CH(OR)$, wherein R is an alkyl group such as methyl, ethyl, or the like, to provide 1b.

Compound 1b is converted to carboxylic acid 1d via a three step sequence including intramolecular cyclization upon heating at reflux in Dowtherm or diphenyl ether (step b), followed by removal (if needed) of the blocking halo group (step c) under palladium-catalyzed dehalogenation conditions and acid- or base-catalyzed saponification (step d). The order of the deprotection and saponification steps can be reversed; i.e., step c can occur before or after step d, as depicted in Scheme 1.

Referring again to Scheme 1, aniline derivative 2c can be prepared from nitrobenzene 2a via a three step sequence. Thus, coupling of nitrobenzene 2a with a cyclic amine 3 as defined herein in the presence of triethylamine provides compound 2b. Palladium-catalyzed reduction of 2b provides amine 2c.

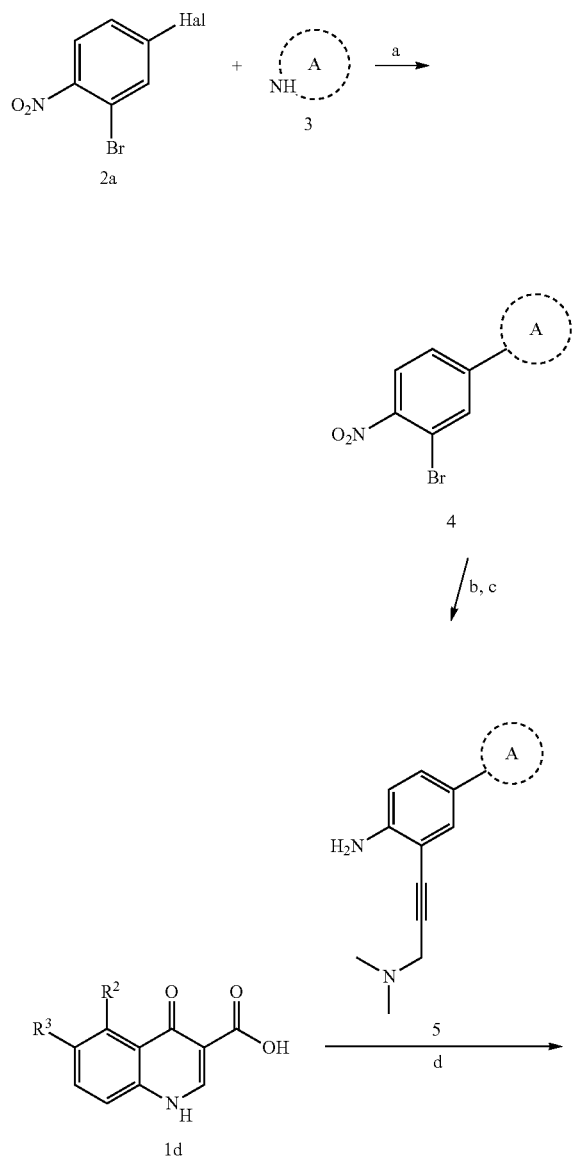

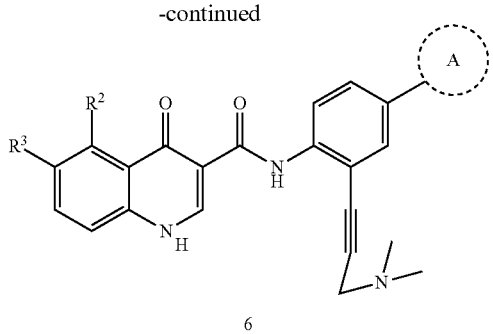

a DMSO, $K_2CO_3$, 80° C.;
b N,N-dimethylprop-2-yn-1-amine, $Pd(PPh_3)_2Cl_2$, CuI, DMF, TEA, 80° C.;
c Fe, $FeSO_4$, $H_2O$ or Zn, AcOH, $H_2O$;
d HATU, $Et_3N$, DMF or propyl phosphonic acid cyclic anhydride (T3P®), pyridine, 2-methyltetrahydrofuran.

Scheme 2 depicts the synthesis of compounds of Formula (I) bearing a propynyl amine sidechain. Thus, coupling of nitrobenzene 2a, wherein Hal is bromide, chloride, or the like, with 3 as defined herein in the presence potassium carbonate in DMSO provides compound 4. Palladium-catalyzed coupling of compound 4 with N,N-dimethylprop-2-yn-1-amine, followed by iron or zinc catalyzed reduction of the nitro moiety, provides amine 5. Coupling of amine 5 with carboxylic acid 1d provides compound 6 which is a compound of Formula (I).

Scheme 3. Preparation of Compounds of Formula (I) Where R is H or OH

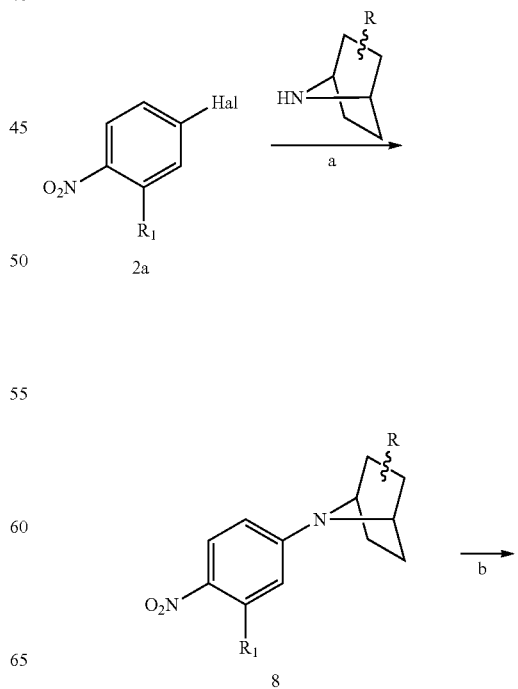

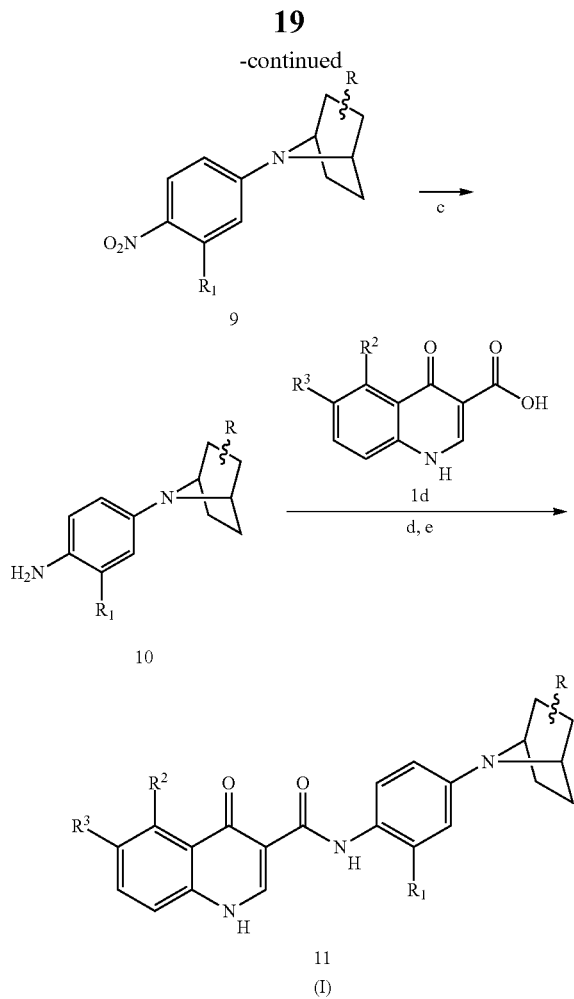

a DMSO, K₂CO₃, heat or CH₃CN, TEA, heat;
b PGX such as TBDMSCl, base such as imidazole, DMF;
c H₂, Pd/C, EtOH;
d HATU, Et₃N, DMF or propyl phosphonic acid cyclic anhydride (T3P®), pyridine, 2-methyltetrahydrofuran;
e deprotection of PG, such as HCl, EtOH. PG = Protecting group; X = leaving group.

Scheme 3 depicts the synthesis of a compound of Formula (I) wherein

3 is 7-azabicyclo[2.2.1]heptane, optionally bearing an exo or endo hydroxy group at the 2-position. The hydroxy-substituted adducts (+)-endo-7-azabicyclo[2.2.1]heptan-2-ol, (−)-endo-7-azabicyclo[2.2.1]heptan-2-ol, (+)-exo-7-azabicyclo[2.2.1]heptan-2-ol, and (−)-exo-7-azabicyclo[2.2.1]heptan-2-ol can be prepared using procedures as described in Fletcher, S. R., et al., "Total Synthesis and Determination of the Absolute Configuration of Epibatidine," *J. Org. Chem*, 59, pp. 1771-1778 (1994). 7-Azabicyclo[2.2.1]heptane itself is commercially available from Tyger Scientific Inc. 324 Stokes Avenue Ewing, N.J., 08638 USA.

Thus, as with the series of transformations summarized in Schemes 1 and 2, coupling of compound 2a with the bicyclo[2.2.1]amine 7 provides compound 8. If a hydroxy group is present in compound 8, it may be necessary to protect the hydroxy group with a protecting group prior to subsequent transformations. Thus, treatment of compound 8 with tert-butyl dimethylsilyl chloride using known conditions provides the protected compound 9 prior to reduction of the nitro moiety to provide the amine 10. Amide formation with 1d (cf. Scheme 3) and removal of the hydroxy protecting group (as needed) provides compound 11 which is a compound of Formula (I).

Uses, Formulation and Administration

Pharmaceutically Acceptable Compositions

In one aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺(C$_{1-4}$alkyl)$_4$ salts. This invention also envisions the quatemization of any basic nitrogen-containing groups of the compounds disclosed herein. Water or oil-soluble or dispersible products may be obtained by such quatemization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a compound of Formula (I) to a subject, preferably a mammal, in need thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gasgtro-esophageal reflux disease, gastrointestinal malignancies, inflammatory bowel disease, constipation, diabetes, arthritis, osteoporosis, and osteopenia.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of the diseases, disorders or conditions as recited above.

The compounds and compositions, according to the method of the present invention, may be administered using any amount and any route of administration effective for treating or lessening the severity of one or more of the diseases, disorders or conditions as recited above.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, a bronchodialator, an anti-biotic, an anti-infective agent, an anti-inflammatory agent, a CFTR modulator other than a compound of the present invention, or a nutritional agent. In a further embodiment, the additional agent is a CFTR modulator other than a compound of the present invention.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example in PCT Publication No. WO2009/074575, the entire contents of which are incorporated herein in their entirety.

Amongst other diseases described herein, combinations of CFTR modulators, such as compounds of Formula I, and agents that reduce the activity of ENaC are use for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as compounds of Formula I, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of CFTR modulators, such as compounds of Formula I, and agents that reduce the activity of ENaC are useful for the treatment of bronchitis of whatever type or genesis including, e.g., acute, arachidic, catarrhal, croupus, chronic or phthinoid bronchitis.

In another embodiment, the additional agent is a CFTR modulator other than a compound of formula I, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026;

and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of Formula (I) or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with a compound of Formula (I). In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of Formula (I).

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells." *Biophys J* 69(4): 1272-80, and Gonzalez, J. E. and R. Y. Tsien (1997); "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising a compound of Formula (I) or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of a composition of Formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

Processes and Intermediates for Making Compounds of Formula (I)

Another aspect of the invention relates to a process for preparing a compound of Formula (Ic):

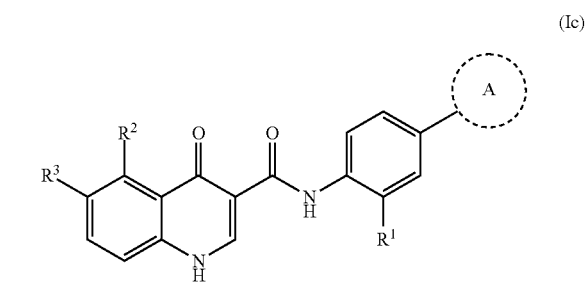

(Ic)

or pharmaceutically acceptable salts thereof, wherein the process comprises:

(a) reacting the acid of formula 1d with an amine of formula 2c to provide a compound of Formula (Ic)

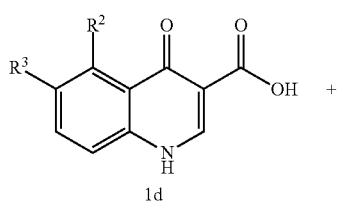

1d

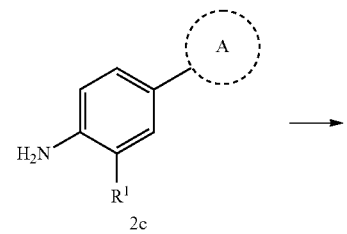

2c

-continued

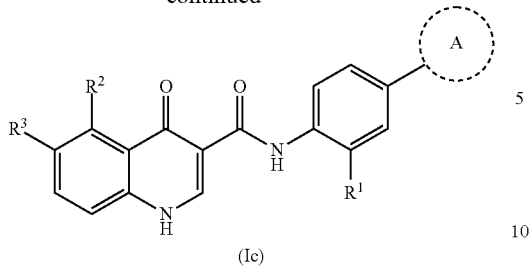

(Ic)

wherein:
Ring A is selected from:

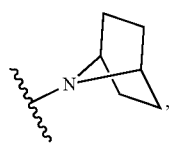

(a)

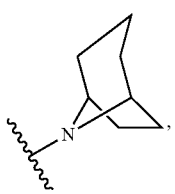

(b)

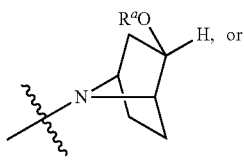

(c)

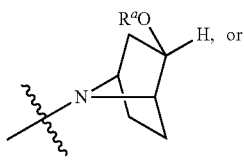

(d)

wherein
R¹ is —CF₃, —CN, or —C≡CCH₂N(CH₃)₂;
R² is hydrogen, —CH₃, —CF₃, —OH, or —CH₂OH;
R³ is hydrogen, —CH₃, —OCH₃, or —CN;
provided that both R² and R³ are not simultaneously hydrogen, and
R$^a$ is hydrogen or a silyl protecting group selected from the group consisting of trimethylsilyl (TMS), tert-butyldiphenylsilyl (TBDPS), tert-butyldimethylsilyl (TBDMS), triisopropylsilyl (TIPS), and [2-(trimethylsilyl)ethoxy]methyl (SEM).

In one embodiment, the reaction of the acid of formula 1d with the amine of formula 2c occurs in a solvent in the presence of O-(7-azabenzotriazol-1-yl)-N,N,N',N'-tetramethyluronium hexafluorophosphate (HATU) and triethylamine or in a solvent in the presence of propyl phosphonic acid cyclic anhydride (T3P®) and pyridine. More particularly, the solvent comprises N,N-dimethyl formamide, ethyl acetate, or 2-methyltetrahydrofuran.

In another embodiment, R$^a$ is hydrogen or TBDMS.
In another embodiment, R$^a$ is TBDMS.

In another embodiment, the process comprises a further deprotection step; for instance, when ring A is

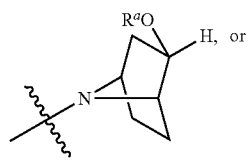

(c)

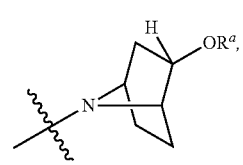

(d)

wherein R$^a$ is a silyl protecting group, to generate a compound of Formula (Ic), wherein ring A is

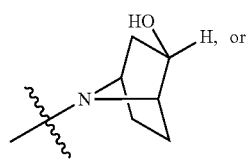

(c)

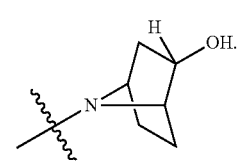

(d)

Typically, removal of a silyl protecting group requires treatment with acid such as acetic acid or a dilute mineral acid or the like, although other reagents, such as a source of fluoride ion (e.g., tetrabutylammonium fluoride), may be used.

In the process, the amine of formula 2c is prepared from a compound of formula 2a comprising the steps of:
(a) reacting the compound of formula 2a with an amine of formula 3 to provide the compound of formula 2b

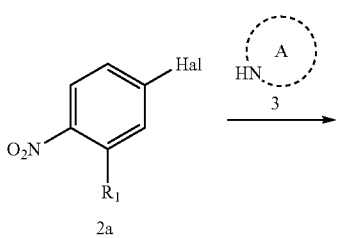

2a

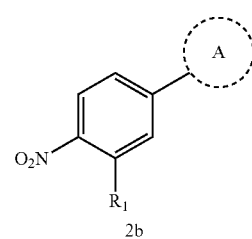

2b wherein:
Hal is F, Cl, Br, or I; and
the amine of formula 3 is

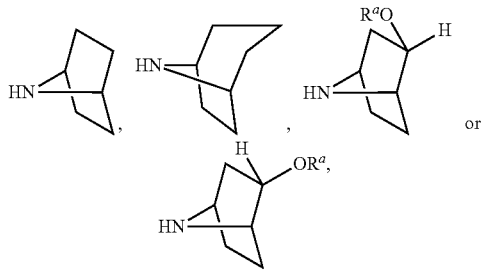

and
(b) reducing the compound of formula 2b to the amine of formula 2c.

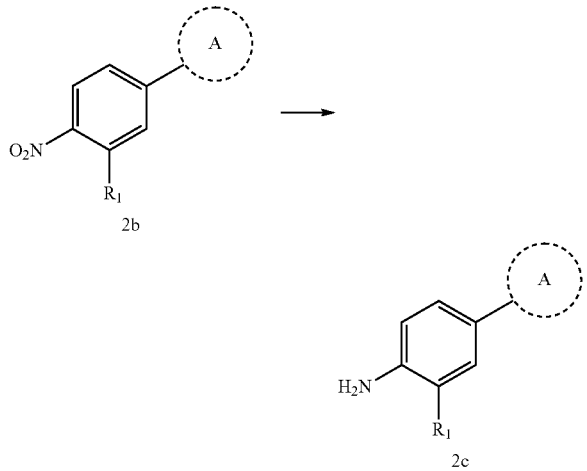

In one embodiment of the process for making the amine of formula 2c, the amine of formula 3 in step (a) is generated in situ from the corresponding quaternary ammonium salt, such as an amine hydrochloride salt, although other ammonium salts (e.g. the trifluoracetate salt), may be used as well.

In one embodiment of step (a) for forming the amine of formula 2c, when the amine of formula 3 is

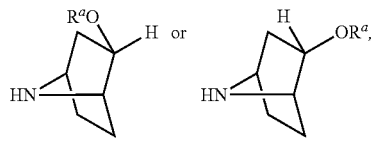

$R^a$ is hydrogen or TBDMS. More particularly, $R^a$ is TBDMS.

In another embodiment, step (a) occurs in a polar aprotic solvent in the presence of a tertiary amine base. Examples of tertiary amines that can be employed include triethylamine, diisopropylethyl amine, 1,5-diazabicyclo[4.3.0]non-5-ene (DBN), 1,8-diazabicyclo[5.4.0]undec-7-ene (DBU), 1,4-diazabicyclo[2.2.2]octane (DABCO) and pyridine. Examples of solvents that can be employed include N,N-dimethyl formamide, dimethyl sulfoxide or acetonitrile.

In one embodiment, the tertiary amine base is triethylamine.

In another embodiment, step (a) occurs in acetonitrile in the presence of triethylamine.

In another embodiment, the reaction temperature of step (a) is between approximately 75° C. and approximately 85° C.

In another embodiment, the reaction time for step (a) is between approximately 2 and approximately 30 hours.

In one embodiment of the process for making the amine of formula 2c, step (b) occurs in a polar protic solvent or a mixture of polar protic solvents in the presence of a palladium catalyst. When palladium is the catalyst, the solvent in step (b) typically is a polar protic solvent such as an alcohol. More particularly, comprises methanol or ethanol.

In another embodiment, step (b) occurs in a polar protic solvent, such as water, in the presence of Fe and $FeSO_4$ or Zn and AcOH.

Another aspect of the invention relates to a process for preparing a compound of Formula (Ic):

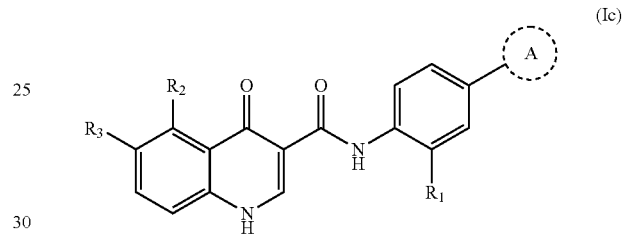

or pharmaceutically acceptable salts thereof, comprising the steps of:
(a) reacting a compound of formula 2a with an amine of formula 3 to provide a compound of formula 2b

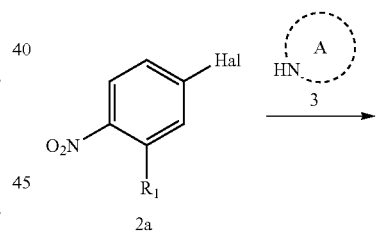

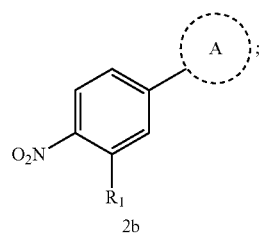

(b) converting the compound of formula 2b to the amine of formula 2c via reduction

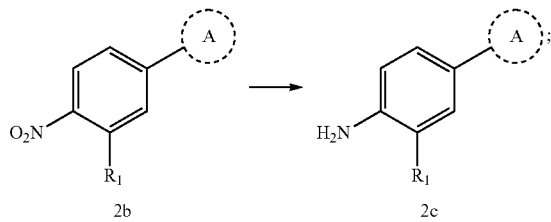

and (c) reacting the amine of formula 2c with an acid of formula 1d to provide a compound of Formula (Ic)

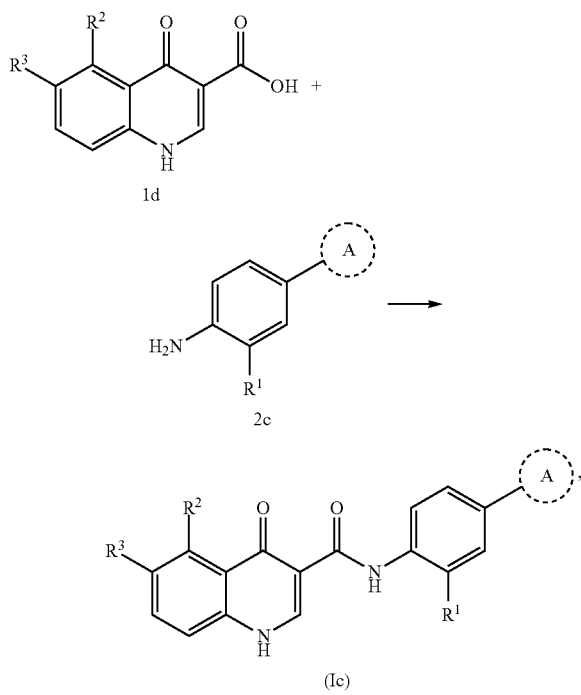

wherein Hal is F, Cl, Br, or I;
the amine of formula 3 is

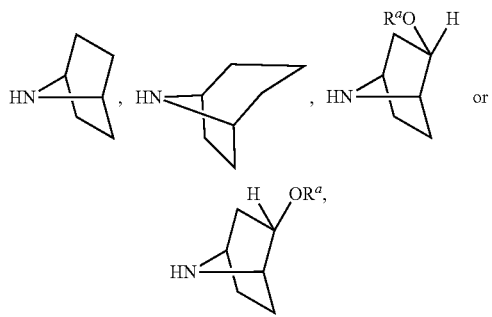

and
ring A is selected from:

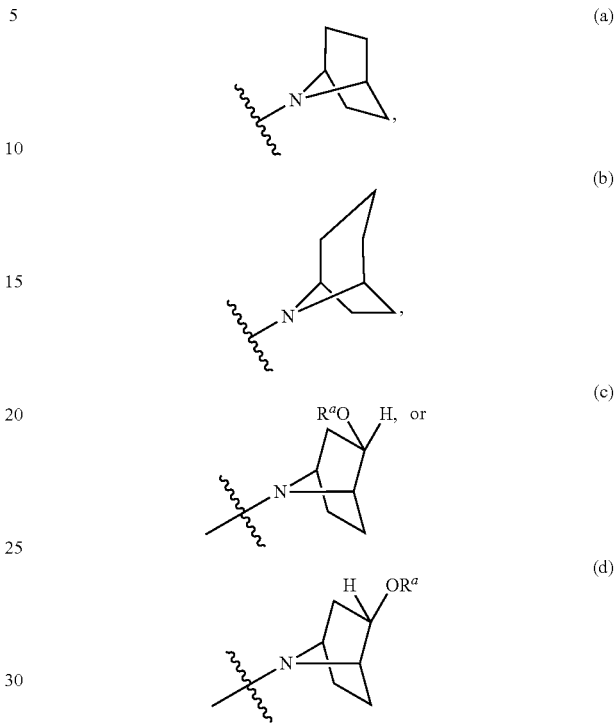

wherein
$R^1$ is —$CF_3$, —CN, or —C≡$CH_2$N$(CH_3)_2$;
$R^2$ is hydrogen, —$CH_3$, —$CF_3$, —OH, or —$CH_2OH$;
$R^3$ is hydrogen, —$CH_3$, —$OCH_3$, or —CN;
provided that both $R^2$ and $R^3$ are not simultaneously hydrogen, and
$R^a$ is hydrogen or a silyl protecting group selected from the group consisting of trimethylsilyl (TMS), tert-butyldiphenylsilyl (TBDPS), tert-butyldimethylsilyl (TBDMS), triisopropylsilyl (TIPS), and [2-(trimethylsilyl)ethoxy]methyl (SEM).

In one embodiment, the amine of formula 3 in step (a) is generated in situ from the corresponding quaternary ammonium salt, such as an amine hydrochloride salt, although other ammonium salts (e.g. the trifluoracetate salt), may be used as well.

In one embodiment of step (a) for forming the amine of formula 2c, when the amine of formula 3 is $R^a$ is hydrogen or TBDMS. More particularly, $R^a$ is TBDMS.

In another embodiment, step (a) occurs in a polar aprotic solvent in the presence of a tertiary amine base. Examples of tertiary amines that can be employed include triethylamine, diisopropylethyl amine, 1,5-diazabicyclo[4.3.0]non-5-ene (DBN), 1,8-diazabicyclo[5.4.0]undec-7-ene (DBU), 1,4-diazabicyclo[2.2.2]octane (DABCO) and pyridine.

In one embodiment, the tertiary amine base is triethylamine.

In another embodiment, step (a) occurs in acetonitrile in the presence of triethylamine.

In another embodiment, the reaction temperature of step (a) is between approximately 75° C. and approximately 85° C.

In another embodiment, the reaction time for step (a) is between approximately 2 and approximately 30 hours.

In one embodiment of the process for making the amine of formula 2c, step (b) occurs in a polar protic solvent or a mixture of polar protic solvents in the presence of a palladium catalyst. When palladium is the catalyst, the solvent in step (b) typically is a polar protic solvent such as an alcohol. More particularly, the solvent comprises methanol or ethanol.

In another embodiment, step (b) occurs in a polar protic solvent, such as water, in the presence of Fe and $FeSO_4$ or Zn and AcOH.

In one embodiment of step (c), the reaction of the acid of formula 1d with the amine of formula 2c occurs in a solvent in the presence of O-(7-azabenzotriazol-1-yl)-N,N,N',N'-tetramethyluronium hexafluorophosphate (HATU) and triethylamine or in a solvent in the presence of propyl phosphonic acid cyclic anhydride (T3P®) and pyridine. More particularly, the solvent comprises N,N-dimethyl formamide, ethyl acetate, or 2-methyltetrahydrofuran.

In another embodiment, $R^a$ is hydrogen or TBDMS.

In another embodiment, $R^a$ is TBDMS.

In another embodiment, the process comprises a further deprotection step; for instance, when ring A is

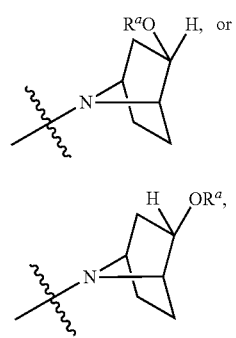

(c)

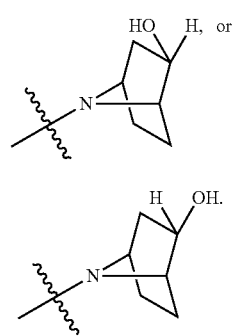

(d)

wherein $R^a$ is a silyl protecting group, to generate a compound of Formula (I), wherein ring A is (c)

(d)

Typically, removal of a silyl protecting group requires treatment with acid such as acetic acid or a dilute mineral acid or the like, although other reagents, such as a source of fluoride ion (e.g., tetrabutylammonium fluoride), may be used.

Another aspect of the invention relates to a compound which is

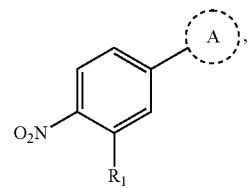

wherein ring A is

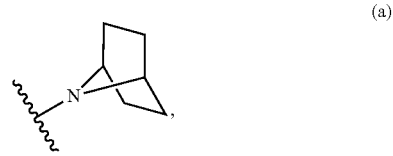
(a)

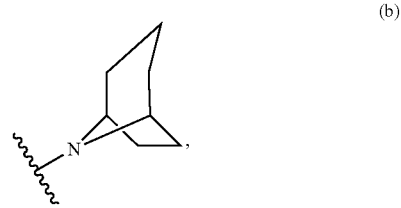
(b)

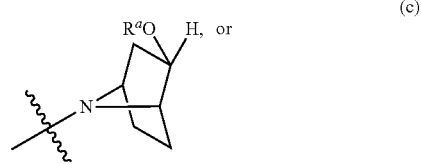
(c)

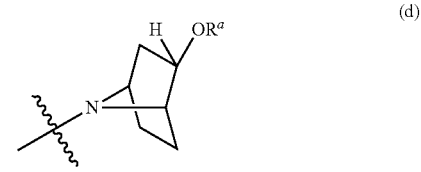
(d)

wherein
$R^1$ is —$CF_3$, —CN, or —C≡$CCH_2N(CH_3)_2$, and
$R^a$ is a silyl protecting group selected from the group consisting of trimethylsilyl (TMS), tert-butyldiphenylsilyl (TBDPS), tert-butyldimethylsilyl (TBDMS), triisopropylsilyl (TIPS), and [2-(trimethylsilyl)ethoxy]methyl (SEM).

Another aspect of the invention relates to a compound which is

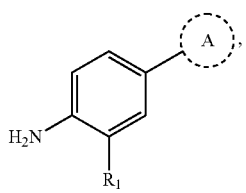

wherein ring A is

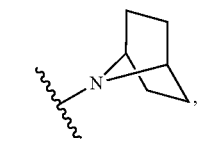
(a)

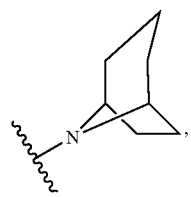
(b)

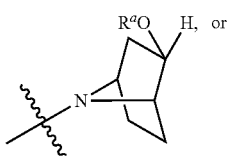
(c)

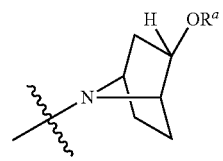
(d)

wherein
R¹ is —CF₃, —CN, or —C≡CCH₂N(CH₃)₂, and
Rᵃ is a silyl protecting group selected from the group consisting of trimethylsilyl (TMS), tert-butyldiphenylsilyl (TBDPS), tert-butyldimethylsilyl (TBDMS), triisopropylsilyl (TIPS), and [2-(trimethylsily)ethoxy]methyl (SEM).

Another aspect of the invention relates to a compound of Formula (IA):

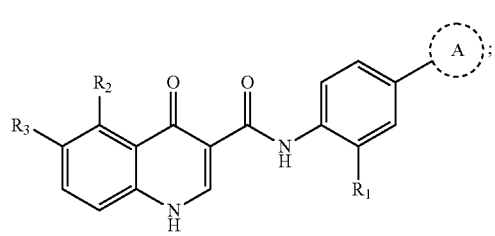
(IA)

or pharmaceutically acceptable salts thereof, wherein:

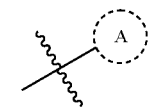

is selected from

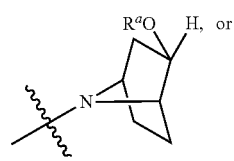
(c)

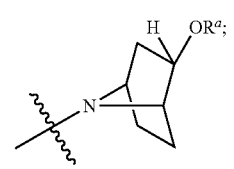
(d)

wherein
R¹ is —CF₃, —CN, or —C≡CH₂N(CH₃)₂;
R² is hydrogen, —CH₃, —CF₃, —OH, or —CH₂OH;
R³ is hydrogen, —CH₃, —OCH₃, or —CN;
  provided that both R² and R³ are not simultaneously hydrogen, and
Rᵃ is a silyl protecting group selected from the group consisting of trimethylsilyl (TMS), tert-butyldiphenylsilyl (TBDPS), tert-butyldimethylsilyl (TBDMS), triisopropylsilyl (TIPS), and [2-(trimethylsilyl)ethoxy]methyl (SEM).

Another aspect of the invention relates to a compound of Formula (I)

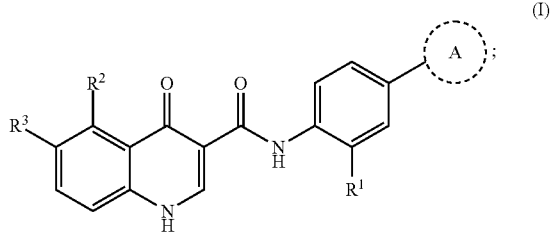
(I)

or pharmaceutically acceptable salts thereof, wherein:
Ring A is selected from:

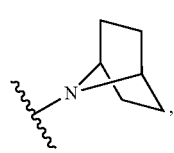
(a)

-continued
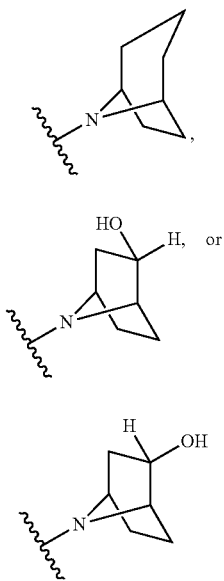
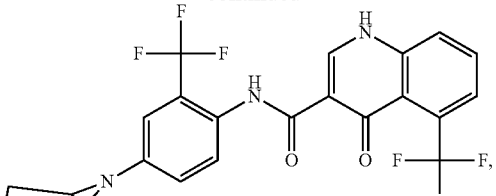
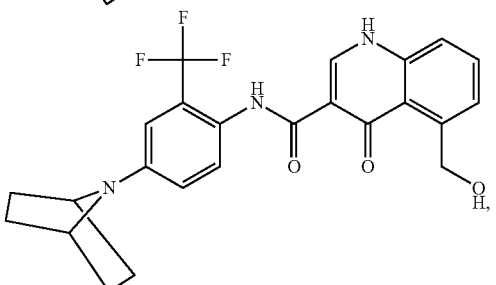
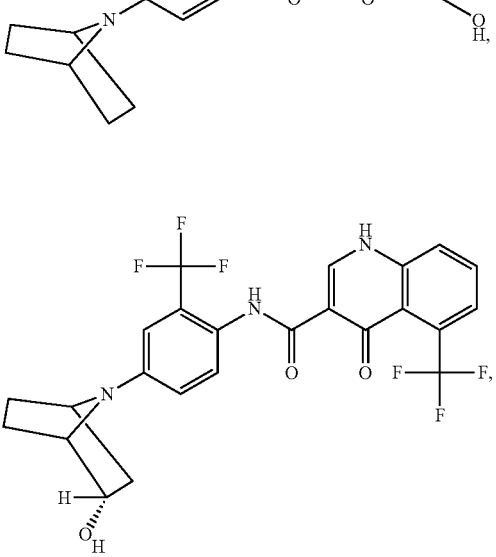
wherein
R¹ is —CF₃, —CN, or —C≡CH₂N(CH₃)₂;
R² is hydrogen, —CH₃, —CF₃, —OH, or —CH₂OH;
R³ is hydrogen, —CH₃, —OCH₃, or —CN;
   provided that both R² and R³ are not simultaneously hydrogen;
made by any of the processes disclosed herein.
Another aspect of the invention relates to a compound selected from the group consisting of:
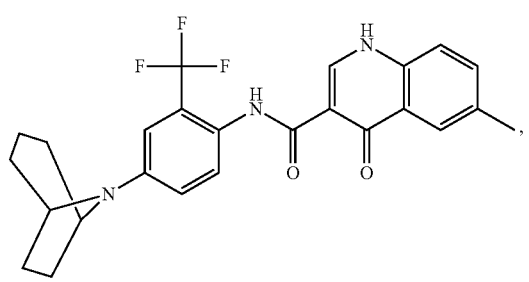
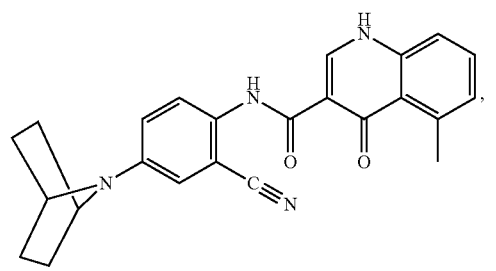
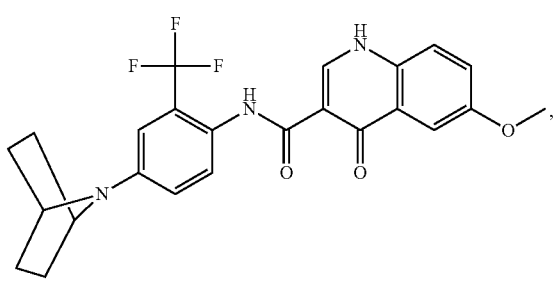
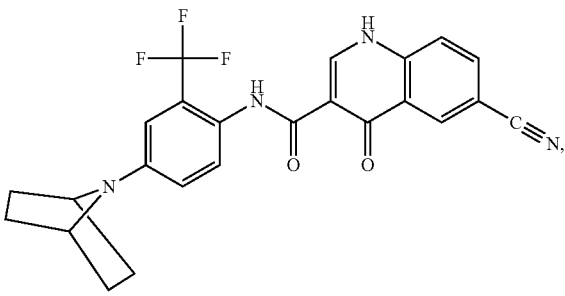

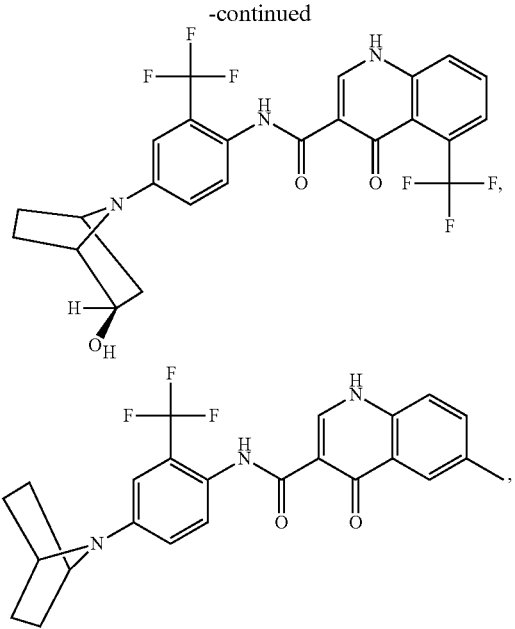
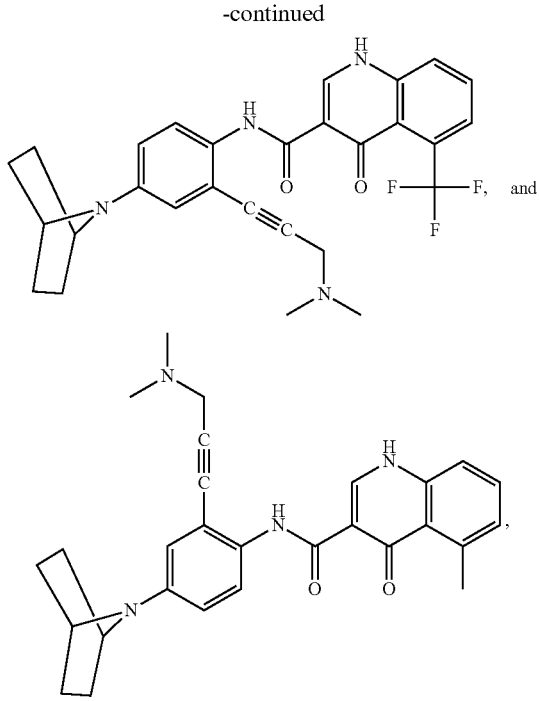
made by any of the processes disclosed herein.
EXAMPLES
Intermediate 1
4-oxo-5-(trifluoromethyl)-1,4-dihydroquinoline-3-carboxylic acid (17)
The synthesis of the title compound is depicted in Scheme 4.
Scheme 4
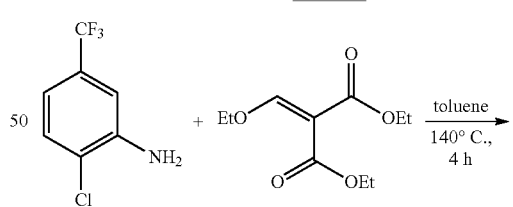
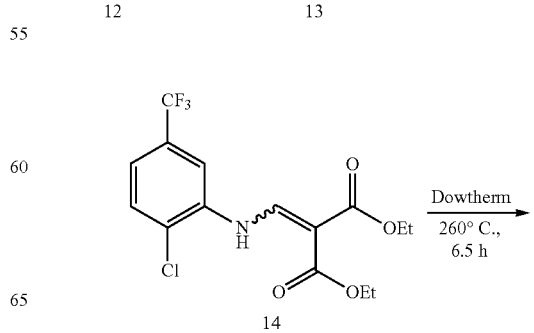

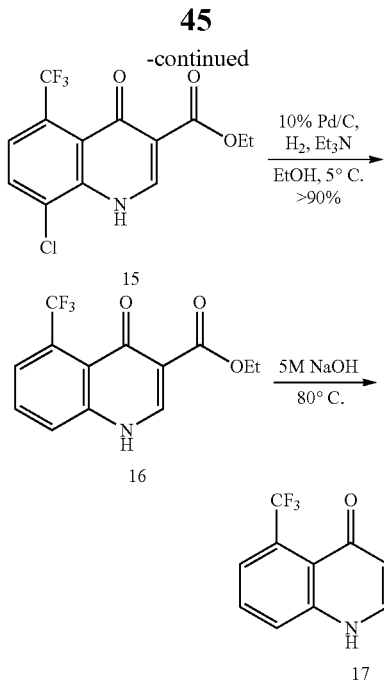

Preparation of diethyl 2-((2-chloro-5-(trifluoromethyl)phenylamino) methylene)malonate (14)

2-Chloro-5-(trifluoromethyl)aniline 12 (200 g, 1.023 mol), diethyl 2-(ethoxymethylene)malonate 13 (276 g, 1.3 mol) and toluene (100 mL) were combined under a nitrogen atmosphere in a three-neck, 1-L round bottom flask equipped with Dean-Stark condenser. The solution was heated with stirring to 140° C. and the temperature was maintained for 4 h. The reaction mixture was cooled to 70° C. and hexane (600 mL) was slowly added. The resulting slurry was stirred and allowed to warm to room temperature. The solid was collected by filtration, washed with 10% ethyl acetate in hexane (2×400 mL) and then dried under vacuum to provide a white solid (350 g, 94% yield) as the desired condensation product diethyl 2-((2-chloro-5-(trifluoromethyl)phenylamino) methylene) malonate 14. $^1$H NMR (400 MHz, DMSO-$d_6$) δ 11.28 (d, J=13.0 Hz, 1H), 8.63 (d, J=13.0 Hz, 1H), 8.10 (s, 1H), 7.80 (d, J=8.3 Hz, 1H), 7.50 (dd, J=1.5, 8.4 Hz, 1H), 4.24 (q, J=7.1 Hz, 2H), 4.17 (q, J=7.1 Hz, 2H), 1.27 (m, 6H).

Preparation of ethyl 8-chloro-4-oxo-5-(trifluoromethyl)-1,4-dihydroquinoline-3-carboxylate (15)

A 3-neck, 1-L flask was charged with Dowtherm® (200 mL, 8 mL/g), which was degassed at 200° C. for 1 h. The solvent was heated to 260° C. and charged in portions over 10 min with diethyl 2-((2-chloro-5-(trifluoromethyl)phenylamino) methylene)malonate 14 (25 g, 0.07 mol). The resulting mixture was stirred at 260° C. for 6.5 hours (h) and the resulting ethanol byproduct removed by distillation. The mixture was allowed to slowly cool to 80° C. Hexane (150 mL) was slowly added over 30 minutes (min), followed by an additional 200 mL of hexane added in one portion. The slurry was stirred until it had reached room temperature. The solid was filtered, washed with hexane (3×150 mL), and then dried under vacuum to provide ethyl 8-chloro-4-oxo-5-(trifluoromethyl)-1,4-dihydroquinoline-3-carboxylate 15 as a tan solid (13.9 g, 65% yield). $^1$H NMR (400 MHz, DMSO-$d_6$) δ 11.91 (s, 1H), 8.39 (s, 1H), 8.06 (d, J=8.3 Hz, 1H), 7.81 (d, J=8.4 Hz, 1H), 4.24 (q, J=7.1 Hz, 2H), 1.29 (t, J=7.1 Hz, 3H).

Preparation of ethyl 4-oxo-5-(trifluoromethyl)-1H-quinoline-3-carboxylate (16)

A 3-neck, 5-L flask was charged with of ethyl 8-chloro-4-oxo-5-(trifluoromethyl)-1,4-dihydroquinoline-3-carboxylate 15 (100 g, 0.3 mol), ethanol (1250 mL, 12.5 mL/g) and triethylamine (220 mL, 1.6 mol). The vessel was then charged with 10 g of 10% Pd/C (50% wet) at 5° C. The reaction was stirred vigorously under hydrogen atmosphere for 20 h at 5° C., after which time the reaction mixture was concentrated to a volume of approximately 150 mL. The product, ethyl 4-oxo-5-(trifluoromethyl)-1H-quinoline-3-carboxylate 16, as a slurry with Pd/C, was taken directly into the next step.

Preparation of 4-oxo-5-(trifluoromethyl)-1,4-dihydroquinoline-3-carboxylic acid (17)

Ethyl 4-oxo-5-(trifluoromethyl)-1H-quinoline-3-carboxylate 16 (58 g, 0.2 mol, crude reaction slurry containing Pd/C) was suspended in NaOH (814 mL of 5 M, 4.1 mol) in a 1-L flask with a reflux condenser and heated at 80° C. for 18 h, followed by further heating at 100° C. for 5 h. The reaction was filtered warm through packed Celite to remove Pd/C and the Celite was rinsed with 1 N NaOH. The filtrate was acidified to about pH 1 to obtain a thick, white precipitate. The precipitate was filtered then rinsed with water and cold acetonitrile. The solid was then dried under vacuum to provide 4-oxo-5-(trifluoromethyl)-1,4-dihydroquinoline-3-carboxylic acid 17 as a white solid (48 g, 92% yield). $^1$H NMR (400.0 MHz, DMSO-$d_6$) δ 15.26 (s, 1H), 13.66 (s, 1H), 8.98 (s, 1H), 8.13 (dd, J=1.6, 7.8 Hz, 1H), 8.06-7.99 (m, 2H).

Intermediate 2

4-(7-azabicyclo[2.2.1]heptan-7-yl)-2-(trifluoromethyl)aniline (21)

The synthesis of the title compound is depicted in Scheme 5.

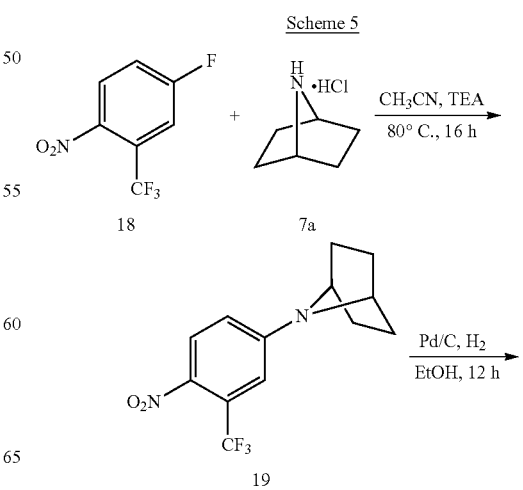

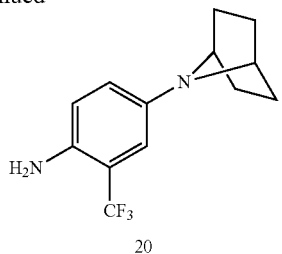

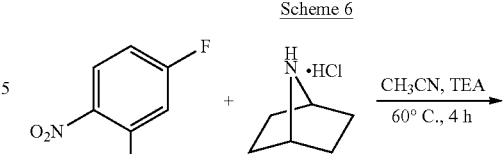

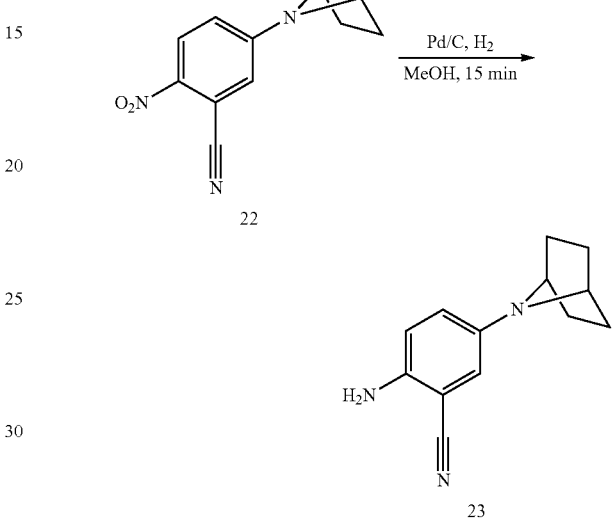

Preparation of 7-[4-nitro-3-(trifluoromethyl)phenyl]-7-azabicyclo[2.2.1]heptane (20)

To a flask containing 7-azabicyclo[2.2.1]heptane hydrochloride 7a (4.6 g, 34.43 mmol, obtained from Tyger Scientific Inc., 324 Stokes Avenue, Ewing, N.J., 08638 USA under a nitrogen atmosphere was added a solution of 4-fluoro-1-nitro-2-(trifluoromethyl)benzene 18 (6.0 g, 28.69 mmol) and triethylamine (8.7 g, 12.00 mL, 86.07 mmol) in acetonitrile (50 mL). The reaction flask was heated at 80° C. under a nitrogen atmosphere for 16 h. The reaction mixture was allowed to cool and then was partitioned between water and dichloromethane. The organic layer was washed with 1 M HCl, dried over $Na_2SO_4$, filtered, and concentrated to dryness. Purification by silica gel chromatography (0-10% ethyl acetate in hexanes) yielded 7-[4-nitro-3-(trifluoromethyl)phenyl]-7-azabicyclo[2.2.1]heptane 19 (7.2 g, 88% yield) as a yellow solid. $^1$H NMR (400.0 MHz, DMSO-$d_6$) δ 8.03 (d, J=9.1 Hz, 1H), 7.31 (d, J=2.4 Hz, 1H), 7.25 (dd, J=2.6, 9.1 Hz, 1H), 4.59 (s, 2H), 1.69-1.67 (m, 4H), 1.50 (d, J=7.0 Hz, 4H).

Preparation of 4-(7-azabicyclo[2.2.1]heptan-7-yl)-2-(trifluoromethyl)aniline (20)

A flask charged with 7-[4-nitro-3-(trifluoromethyl)phenyl]-7-azabicyclo[2.2.1]heptane 19 (7.07 g, 24.70 mmol) and 10% Pd/C (0.71 g, 6.64 mmol) was evacuated and then flushed with nitrogen. Ethanol (22 mL) was added and the reaction flask was fitted with a hydrogen balloon. After stirring vigorously for 12 h, the reaction mixture was purged with nitrogen and Pd/C was removed by filtration. The filtrate was concentrated to a dark oil under reduced pressure and the residue purified by silica gel chromatography (0-15% ethyl acetate in hexanes) to provide 4-(7-azabicyclo[2.2.1]heptan-7-yl)-2-(trifluoromethyl)aniline 20 as a purple solid (5.76 g, 91% yield). $^1$H NMR (400.0 MHz, DMSO-$d_6$) δ 6.95 (dd, J=2.3, 8.8 Hz, 1H), 6.79 (d, J=2.6 Hz, 1H), 6.72 (d, J=8.8 Hz, 1H), 4.89 (s, 2H), 4.09 (s, 2H), 1.61-1.59 (m, 4H) and 1.35 (d, J=6.8 Hz, 4H).

Intermediate 3

2-amino-5-(7-azabicyclo[2.2.1]heptan-7-yl)benzonitrile (23)

The synthesis of the title compound is depicted in Scheme 6.

Preparation of 5-(7-azabicyclo[2.2.1]heptan-7-yl)-2-nitrobenzonitrile (22)

To a solution of 5-fluoro-2-nitrobenzonitrile 21 (160 mg, 0.96 mmol) in acetonitrile (1 mL) was slowly added 7-azabicyclo[2.2.1]heptane hydrochloride 7a (129 mg, 0.96 mmol) and triethylamine (244 mg, 335.7 μL, 2.41 mmol). The reaction was stirred at 60° C. for 4 h. The reaction was quenched with water, acidified with 1 N HCl to pH 1, and extracted with dichloromethane (3×10 mL). The combined organic layers were washed with water, dried over $MgSO_4$, filtered and concentrated to provide 5-(7-azabicyclo[2.2.1]heptan-7-yl)-2-nitrobenzonitrile 22 (205 mg, 87% yield). LC/MS m/z 244.3 $[M+H]^+$, retention time 1.69 min (RP-$C_{18}$, 10-99% $CH_3CN/0.05\%$ TFA over 3 min).

Preparation of 2-amino-5-(7-azabicyclo[2.2.1]heptan-7-yl)benzonitrile (23)

A flask charged with 5-(7-azabicyclo[2.2.1]heptan-7-yl)-2-nitrobenzonitrile 22 (205 mg, 0.8427 mmol) and 10% Pd/C (41 mg, 0.39 mmol) was flushed with nitrogen and then evacuated under vacuum. Methanol (4 mL) was added under nitrogen atmosphere and the flask was fitted with a hydrogen balloon. After stirring for 15 min, the Pd/C was removed by filtration and solvent was removed under reduced pressure to provide 2-amino-5-(7-azabicyclo[2.2.1]heptan-7-yl)benzonitrile 23 (170 mg, 95% yield). $^1$H NMR (400.0 MHz, DMSO-$d_6$) δ 7.02 (dd, J=2.8, 9.0 Hz, 1H), 6.87 (d, J=2.7 Hz, 1H), 6.68 (d, J=9.0 Hz, 1H), 5.36 (s, 2H), 4.09 (s, 2H), 1.59 (d, J=6.8 Hz, 4H), 1.34 (d, J=6.8 Hz, 4H).

Intermediate 4

4-(7-azabicyclo[2.2.1]heptan-7-yl)-2-(3-(dimethylamino)prop-1-ynyl)aniline (27)

The synthesis of the title compound is depicted in Scheme 7.

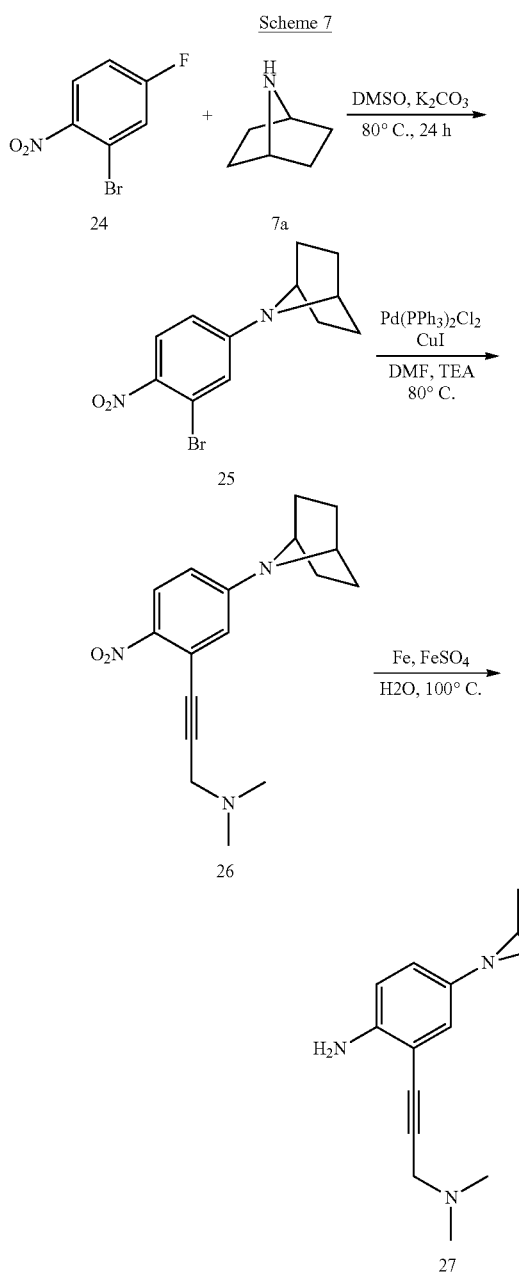

Preparation of 7-(3-bromo-4-nitrophenyl)-7-azabicyclo[2.2.1]heptane (25)

To a solution of 2-bromo-4-fluoro-1-nitro-benzene 24 (1.1 g, 4.8 mmol) and $K_2CO_3$ (2.0 g, 14.3 mmol) in DMSO (8.400 mL) was added 7-azabicyclo[2.2.1]heptane 7a (765.4 mg, 5.7 mmol) portion-wise. The reaction was stirred at 80° C. for 24 h. The reaction was diluted with water to precipitate the product. The solid was redissolved in dichloromethane, washed with 1.0 N HCl, dried over $MgSO_4$, filtered and concentrated to provide 7-(3-bromo-4-nitrophenyl)-7-azabicyclo[2.2.1]heptane 25 (1.1 g, 78% yield). The crude product was used directly in the next step. LC/MS m/z 299.1 [M+H]$^+$, retention time 1.97 min (RP-$C_{18}$, 10-99% $CH_3CN$/0.05% TFA over 3 min).

Preparation of 3-[5-(7-azabicyclo[2.2.1]heptan-7-yl)-2-nitro-phenyl]-N,N-dimethyl-prop-2-yn-1-amine (26)

To 7-(3-bromo-4-nitro-phenyl)-7-azabicyclo[2.2.1]heptane 25 (500 mg, 1.683 mmol), $Pd(PPh_3)_2Cl_2$ (59 mg, 0.08 mmol), and cuprous iodide (9.616 mg, 1.708 µL, 0.05049 mmol) was added a solution of N,N-dimethylprop-2-yn-1-amine (420 mg, 538 µL, 5.05 mmol) in degassed DMF (5 mL) and triethylamine (5 mL). The reaction mixture was microwaved under $N_2$ for 10 min at 100° C. The reaction was diluted with ethyl acetate, washed with 50% saturated sodium bicarbonate solution (2×20 mL), water, and brine. The solution was dried over anhydrous $Na_2SO_4$ and filtered, leaving a red solid. Purification by silica gel chromatography (0-50% dichloromethane in ethyl acetate) yielded 3-[5-(7-azabicyclo[2.2.1]heptan-7-yl)-2-nitro-phenyl]-N,N-dimethyl-prop-2-yn-1-amine 26 (400 mg, 79% yield). LC/MS m/z 300.5 [M+H]$^+$, retention time 1.11 min (RP-$C_{18}$, 10-99% $CH_3CN$/0.05% TFA over 3 min).

Preparation of 4-(7-azabicyclo[2.2.1]heptan-7-yl)-2-(3-dimethylaminoprop-1-ynyl)aniline (27)

3-[5-(7-Azabicyclo[2.2.1]heptan-7-yl)-2-nitro-phenyl]-N,N-dimethyl-prop-2-yn-1-amine 26 (340 mg, 1.14 mmol), iron (634 mg, 11.36 mmol) and ferrous sulfate heptahydrate (316 mg, 1.136 mmol) were suspended in water (1 mL) and refluxed for 20 min. The reaction was filtered and the solid washed with methanol and dichloromethane. The filtrate was concentrated and purified by silica gel chromatography using (0-5% methanol in dichloromethane) to provide 4-(7-azabicyclo[2.2.1]heptan-7-yl)-2-(3-dimethylaminoprop-1-ynyl)aniline 27 (148 mg, 48% yield). LC/MS m/z 270.3 [M+H]$^+$, retention time 0.25 min (RP-$C_{18}$, 10-99% $CH_3CN$/0.05% TFA over 3 min).

Intermediate 5 exo-4-(2-(tert-butyldimethylsilyloxy)-7-azabicyclo[2.2.1]heptan-7-yl)-2-(trifluoromethyl)aniline (30)

The synthesis of the title compound is depicted in Scheme 8.

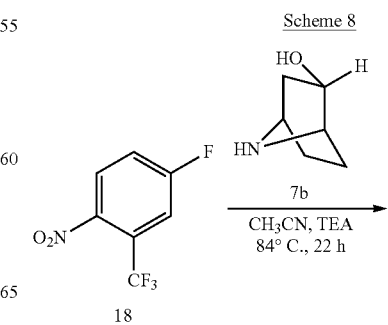

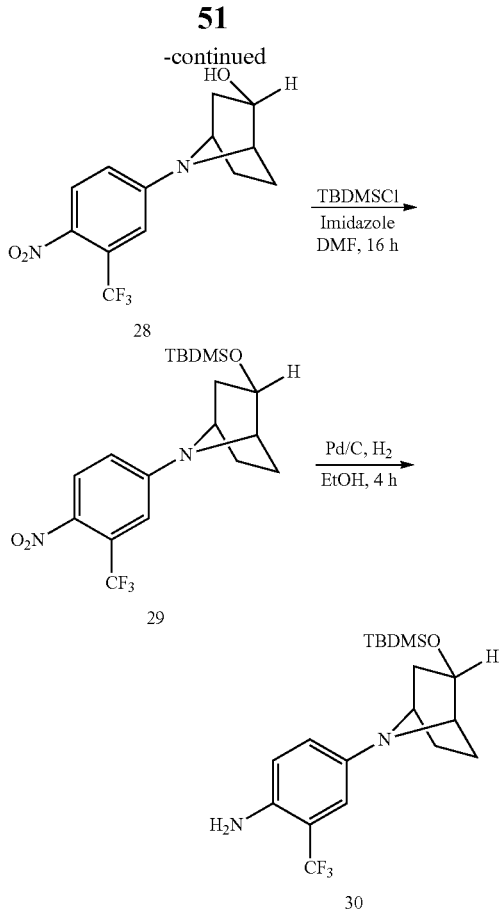

Preparation of exo-7-[4-nitro-3-(trifluoromethyl) phenyl]-7-azabicyclo[2.2.1]heptan-5-ol (28)

To a flask containing exo-7-azabicyclo[2.2.1]heptan-2-ol 7b (0.86 g, 5.74 mmol) under a nitrogen atmosphere was added a solution of 4-fluoro-1-nitro-2-(trifluoromethyl)benzene 18 (1 g, 4.78 mmol) and triethylamine (1.45 g, 2.0 mL, 14.35 mmol) in acetonitrile (8 mL). The reaction was heated at 84° C. under a nitrogen atmosphere for 22 h. The reaction mixture was allowed to cool and then was partitioned between water and ethyl acetate. The layers were separated and the aqueous layer was extracted twice with ethyl acetate. The combined organic layers were dried over $Na_2SO_4$, filtered, and concentrated to dryness. Purification by silica gel chromatography (0-50% ethyl acetate in hexanes) provided exo-7-[4-nitro-3-(trifluoromethyl)phenyl]-7-azabicyclo[2.2.1]heptan-5-ol 28 as a yellow solid (0.67 g, 46% yield). LC/MS m/z 303.3 [M+H]+, retention time 1.51 min (RP-$C_{18}$, 10-99% $CH_3CN$/0.05% TFA over 3 min).

Preparation of exo-tert-butyl-dimethyl-[[7-[4-nitro-3-(trifluoromethyl)phenyl]-7-azabicyclo[2.2.1]heptan-5-yl]oxy]silane 29

Tert-butyl-chloro-dimethyl-silane (197 mg, 1.267 mmol) was added to a solution of 4H-imidazole (144 mg, 2.11 mmol) in DMF (0.5 mL). After the solution stopped bubbling, exo-7-[4-nitro-3-(trifluoromethyl)phenyl]-7-azabicyclo[2.2.1]heptan-5-ol 28 (255 mg, 0.84 mmol) was added as a solution in DMF (0.6 mL) and stirred at room temperature for 14 h. The reaction was quenched with water and extracted twice with diethyl ether, dried over $MgSO_4$, filtered and concentrated to a colorless oil. Purification by silica gel chromatography (0-40% dichloromethane in hexanes) afforded exo-tert-butyl-dimethyl-[[7-[4-nitro-3-(trifluoromethyl)phenyl]-7-azabicyclo[2.2.1]heptan-5-yl]oxy]silane 29 (318 mg, 90% yield) as a yellow oil. $^1$H NMR (400.0 MHz, DMSO-$d_6$) δ 8.01 (d, J=9.2 Hz, 1H), 7.29 (d, J=2.4 Hz, 1H), 7.19 (dd, J=2.6, 9.2 Hz, 1H), 4.60 (t, J=4.4 Hz, 1H), 4.47 (d, J=5.2 Hz, 1H), 4.07 (dd, J=2.0, 6.8 Hz, 1H), 1.94 (dd, J=6.4, 12.8 Hz, 1H), 1.71-1.47 (m, 3H), 1.39-1.32 (m, 2H), 0.65 (s, 9H), 0.03 (s, 6H).

Preparation of exo-4-[5-[tert-butyl(dimethyl)silyl]oxy-7-azabicyclo[2.2.1]heptan-7-yl]-2-(trifluoromethyl)aniline (30)

A flask containing palladium on activated carbon (10 wt %, 30 mg, 0.28 mmol) was evacuated, purged with $N_2$, and charged with a solution of exo-tert-butyl-dimethyl-[[7-[4-nitro-3-(trifluoromethyl)phenyl]-7-azabicyclo[2.2.1]heptan-5-yl]oxy]silane 29 (301 mg, 0.72 mmol) in ethanol (3 mL). The flask was evacuated and then was equipped with a balloon of $H_2$ and stirred for 4 h at room temperature. The mixture was filtered and concentrated to dryness to yield exo-4-[5-[tert-butyl(dimethyl)silyl]oxy-7-azabicyclo[2.2.1]heptan-7-yl]-2-(trifluoromethyl)aniline 30 (268 mg, 96% yield) as an off-white solid. $^1$H NMR (400.0 MHz, DMSO-$d_6$) δ 6.92 (dd, J=2.4, 8.8 Hz, 1H), 6.77 (d, J=2.6 Hz, 1H), 6.70 (d, J=8.8 Hz, 1H), 4.84 (s, 2H), 4.11 (t, J=4.4 Hz, 1H), 3.91-3.89 (m, 2H), 1.82 (dd, J=7.1, 12.3 Hz, 1H), 1.54-1.39 (m, 3H), 1.20-1.16 (m, 2H), 0.79 (s, 9H), 0.02 (s, 6H).

Intermediate 6 endo-4-(2-(tert-butyldimethylsilyloxy)-7-azabicyclo[2.2.1]heptan-7-yl)-2-(trifluoromethyl)aniline (34)

The preparation of the title compound is depicted in Scheme 9.

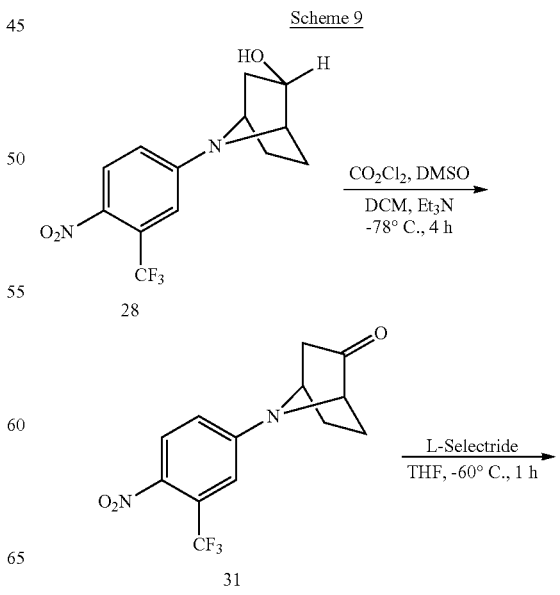

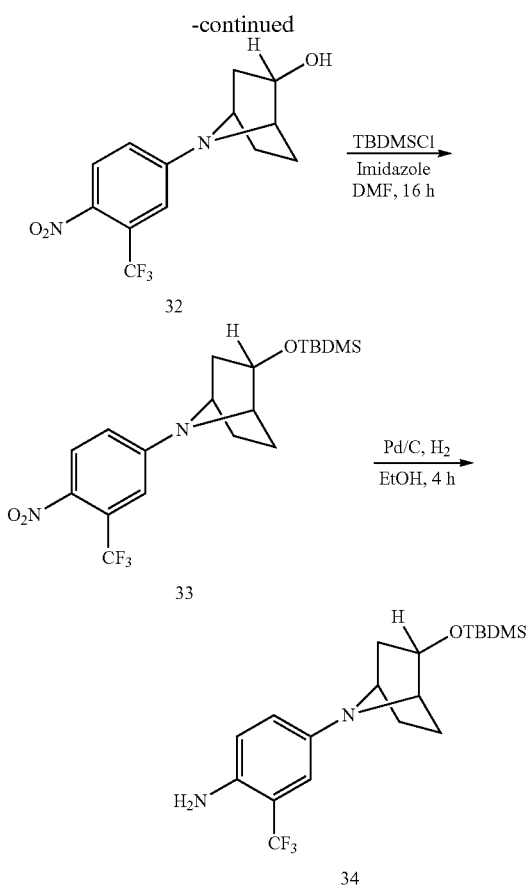

Preparation of 7-azabicyclo[2.2.1]heptan-5-one (31)

To a solution of oxalyl dichloride (165 mg, 113 μL, 1.27 mmol) in dichloromethane (3 mL) under a nitrogen atmosphere at −78° C. was added a solution of DMSO (199 mg, 180 μL, 2.54 mmol) in dichloromethane (0.7 mL) dropwise. The reaction mixture was allowed to stir for 30 min and then a solution of exo-7-[4-nitro-3-(trifluoromethyl)phenyl]-7-azabicyclo[2.2.1]heptan-5-ol 28 (320 mg, 1.06 mmol) in dichloromethane (2.5 mL) was added dropwise. The reaction was stirred for an additional hour at −78° C., and then triethylamine (536 mg, 738 μL, 5.30 mmol) was added dropwise and the reaction was warmed to room temperature. The reaction mixture was diluted with dichloromethane, partitioned between dichloromethane and water, and the layers were separated. The aqueous layer was extracted once more with dichloromethane. The combined organic layers were dried over $Na_2SO_4$, filtered and concentrated to a yellow oil. Purification by silica gel chromatography (0-30% ethyl acetate in hexanes) provided 7-[4-nitro-3-(trifluoromethyl)phenyl]-7-azabicyclo[2.2.1]heptan-5-one 31 (266 mg, 84% yield) as a yellow solid. $^1$H NMR (400.0 MHz, DMSO-$d_6$) δ 8.06 (d, J=9.1 Hz, 1H), 7.47 (d, J=2.4 Hz, 1H), 7.39 (dd, J=2.6, 9.1 Hz, 1H), 4.98 (t, J=4.5 Hz, 1H), 4.84 (d, J=5.4 Hz, 1H), 2.44 (d, J=3.1 Hz, 1H), 2.23 (d, J=16 Hz, 1H), 2.00-1.92 (m, 1H), 1.88-1.70 (m, 2H), 1.66-1.60 (m, 1H).

Preparation of endo-7-[4-nitro-3-(trifluoromethyl)phenyl]-7-azabicyclo[2.2.1]heptan-5-ol (32)

To a solution of 7-[4-nitro-3-(trifluoromethyl)phenyl]-7-azabicyclo[2.2.1]heptan-5-one 31 (261 mg, 0.87 mmol) in THF (11 mL) at −55° C. under a nitrogen atmosphere was added a solution of lithium hydrido-trisec-butyl-boron (1.04 mL of 1 M, 1.04 mmol) dropwise. After 30 min, the reaction mixture was transferred to an ice water bath and stirring was continued. The reaction mixture was quenched with methanol (1.2 mL) at 0° C. The reaction mixture was partitioned between dichloromethane/water, separated and the aqueous layer was extracted twice more with dichloromethane. The organic layers were combined, dried over $Na_2SO_4$, filtered, and concentrated to dryness. Purification by silica gel chromatography (0-50% ethyl acetate in hexanes) provided endo-7-[4-nitro-3-(trifluoromethyl)phenyl]-7-azabicyclo[2.2.1]heptan-5-ol 32 (222 mg, 84% yield) as a yellow solid. $^1$H NMR (400.0 MHz, DMSO-$d_6$) δ 8.01 (d, J=9.1 Hz, 1H), 7.27 (d, J=3.0 Hz, 1H), 7.22 (dd, J=2.6, 9.1 Hz, 1H), 5.17 (d, J=4.4 Hz, 1H), 4.49 (t, J=4.9 Hz, 1H), 4.44 (t, J=4.5 Hz, 1H), 4.16-4.10 (m, 1H), 2.20-2.06 (m, 2H), 1.67-1.44 (m, 3H), 1.09 (dd, J=3.5, 12.4 Hz, 1H).

Preparation of endo-tert-butyl-dimethyl-[[7-[4-nitro-3-(trifluoromethyl)phenyl]-7-azabicyclo[2.2.1]heptan-5-yl]oxy]silane (33)

Tert-butylchlorodimethylsilane (168 mg, 1.08 mmol) was added to a solution of 4H-imidazole (122 mg, 1.80 mmol) in DMF (425.3 μL). After the solution stopped bubbling, endo-7-[4-nitro-3-(trifluoromethyl)phenyl]-7-azabicyclo[2.2.1]heptan-5-ol 32 (217 mg, 0.72 mmol) was added as a solution in DMF (1 mL) and stirred at room temperature for 14 h. The reaction was quenched with water and extracted twice with diethyl ether, dried over $MgSO_4$, filtered, and concentrated to a colorless oil. Purification by silica gel chromatography (0-40% dichloromethane in hexanes) afforded endo-tert-butyl-dimethyl-[[7-[4-nitro-3-(trifluoromethyl)phenyl]-7-azabicyclo[2.2.1]heptan-5-yl]oxy]silane 33 (251 mg, 84% yield) as a yellow oil. $^1$H NMR (400.0 MHz, DMSO-$d_6$) δ 8.01 (d, J=9.1 Hz, 1H), 7.32 (d, J=2.3 Hz, 1H), 7.26 (dd, J=2.5, 9.1 Hz, 1H), 4.54-4.51 (m, 2H), 4.29-4.26 (m, 1H), 2.20-2.11 (m, 2H), 1.67-1.45 (m, 3H), 1.08 (dd, J=3.2, 12.4 Hz, 1H), 0.88 (s, 9H), 0.07 (d, J=2.6 Hz, 6H).

Preparation of endo-4-[5-[tert-butyl(dimethyl)silyl]oxy-7-azabicyclo[2.2.1]heptan-7-yl]-2-(trifluoromethyl)aniline (34)

A flask containing palladium on activated carbon (10 wt %, 24 mg, 0.23 mmol) was evacuated and then purged under a nitrogen atmosphere. To this was added a solution of endo-tert-butyl-dimethyl-[[7-[4-nitro-3-(trifluoromethyl)phenyl]-7-azabicyclo[2.2.1]heptan-5-yl]oxy]silane 33 (240 mg, 0.58 mmol) in ethanol (5 mL). The reaction mixture was evacuated, then equipped with a balloon of $H_2$ and stirred for 4 h at room temperature. The mixture was filtered and concentrated to dryness to yield endo-4-[5-[tert-butyl(dimethyl)silyl]oxy-7-azabicyclo[2.2.1]heptan-7-yl]-2-(trifluoromethyl)aniline 34 (222 mg, 100% yield) as an off-white solid. $^1$H NMR (400.0 MHz, DMSO-$d_6$) δ 6.95 (dd, J=2.4, 8.8 Hz, 1H), 6.79 (d, J=2.6 Hz, 1H), 6.72 (d, J=8.8 Hz, 1H), 4.91 (s, 2H), 4.24-4.19 (m, 1H), 4.06-4.03 (m, 2H), 2.12-1.99 (m, 2H), 1.55-1.53 (m, 1H), 1.42-1.36 (m, 2H), 0.96 (dd, J=3.2, 12.2 Hz, 1H), 0.87 (s, 9H), 0.05 (s, 6H).

Example Compound 3

N-(4-(7-azabicyclo[2.2.1]heptan-7-yl)-2-(trifluoromethyl)phenyl)-4-oxo-5-(trifluoromethyl)-1,4-dihydroquinoline-3-carboxamide The preparation of the title compound is depicted in Scheme 10.

Scheme 10

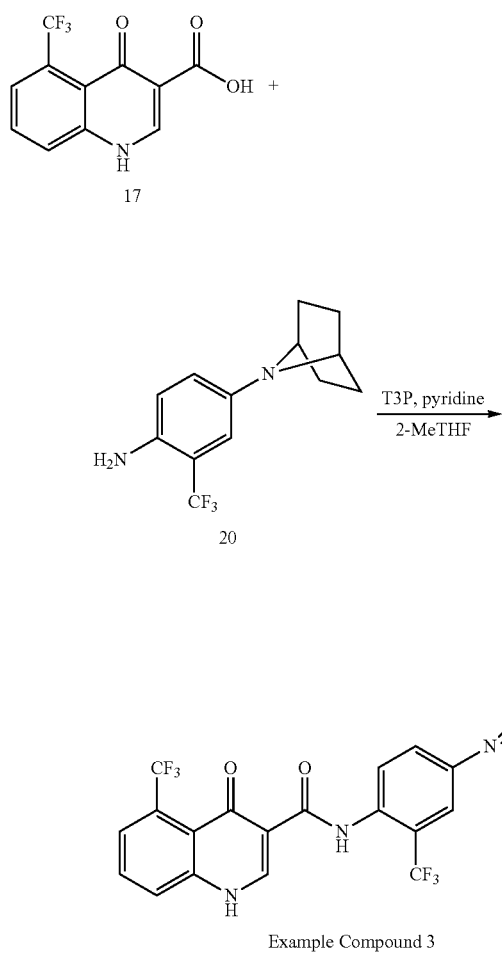

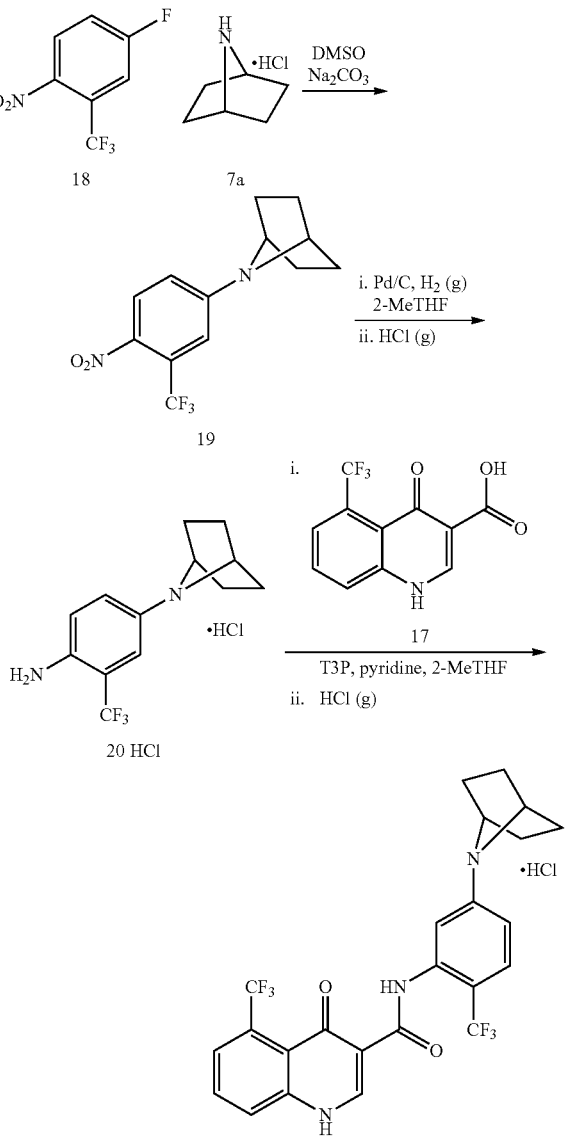

Example Compound 3
Form A Hydrochloride Salt
(Form A-HCl)

To a solution of 4-oxo-5-(trifluoromethyl)-1H-quinoline-3-carboxylic acid 17 (9.1 g, 35.39 mmol) and 4-(7-azabicyclo[2.2.1]heptan-7-yl)-2-(trifluoromethyl)aniline 20 (9.2 g, 35.74 mmol) in 2-methyltetrahydrofuran (91.00 mL) was added propyl phosphonic acid cyclic anhydride (T3P, 50% solution in ethyl acetate, 52.68 mL, 88.48 mmol) and pyridine (5.6 g, 5.73 mL, 70.78 mmol) at room temperature. The reaction flask heated at 65° C. for 10 h under a nitrogen atmosphere. After cooling to room temperature, the reaction was then diluted with ethyl acetate and quenched with saturated $Na_2CO_3$ solution (50 mL). The layers were separated, and the aqueous layer was extracted twice more with ethyl acetate. The combined organic layers were washed with water, dried over $Na_2SO_4$, filtered and concentrated to a tan solid. The crude solid product was slurried in ethyl acetate/diethyl ether (2:1), collected by vacuum filtration, and washed twice more with ethyl acetate/diethyl ether (2:1) to provide the product as a light yellow crystalline powder. The powder was dissolved in warm ethyl acetate and absorbed onto Celite. Purification by silica gel chromatography (0-50% ethyl acetate in dichloromethane) provided N-(4-(7-azabicyclo[2.2.1]heptan-7-yl)-2-(trifluoromethyl)phenyl)-4-oxo-5-(trifluoromethyl)-1,4-dihydroquinoline-3-carboxamide as a white crystalline solid (13.5 g, 76% yield). LC/MS m/z 496.0 [M+H]$^+$, retention time 1.48 min (RP-C$_{18}$, 10-99% $CH_3CN$/0.05% TFA over 3 min). $^1$H NMR (400.0 MHz, DMSO-d$_6$) δ 13.08 (s, 1H), 12.16 (s, 1H), 8.88 (s, 1H), 8.04 (dd, J=2.1, 7.4 Hz, 1H), 7.95-7.88 (m, 3H), 7.22 (dd, 2.5, 8.9 Hz, 1H), 7.16 (d, J=2.5 Hz, 1H), 4.33 (s, 2H), 1.67 (d, J=6.9 Hz, 4H), 1.44 (d, J=6.9 Hz, 4H).

Example Compound 3 Form A HCl Salt

N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Form A-HCl)

Preparation of 7-[4-nitro-3-(trifluoromethyl)phenyl]-7-azabicyclo[2.2.1]heptane (19)

4-fluoro-1-nitro-2-(trifluoromethyl)benzene (18) (901 g) was added into a 30 L jacketed vessel. Sodium carbonate (959.1 g) and 5 L dimethylsulfoxide (DMSO) was added and the mixture was stirred under a nitrogen atmosphere. 7-azabicyclo[2.2.1]heptane hydrochloride (7a) (633.4 g) was added to the vessel in portions. The temperature of the mixture was gradually raised to 55° C., and the reaction was monitored by HPLC. When the substrate was less than 1% AUC, the reaction was considered complete. The mixture was then diluted with 10 vol. 2-methyltetrahydrofuran and washed with 5.5 vol. water three times until no DMSO remained in the aqueous layer as determined by HPLC, to give 7-[4-nitro-3-(trifluoromethyl) phenyl]-7-azabicyclo[2.2.1]heptane (19) in 2-methyltetrahydrofuran (approximately 95% yield).

Preparation of hydrochloride salt of 4-(7-azabicyclo[2.2.1]heptan-7-yl)-2-(trifluoromethyl)aniline (20.HCl)

Palladium on carbon (150 g, 5 w/w) was charged into a Büchi Hydrogenator (20 L capacity) under a nitrogen atmosphere, followed by the addition of 7-[4-nitro-3-(trifluoromethyl) phenyl]-7-azabicyclo[2.2.1]heptane (19) (1500 g) and 2-methyltetrahydrofuran (10.5 L, 7 vol). Hydrogen gas was charged into the closed hydrogenator to a pressure of 0.5 bar. A vacuum was applied for about 2 min, followed by the introduction of hydrogen gas to a pressure of 0.5 bar. This process was repeated 2 times. Hydrogen gas was then continuously charged to the mixture at a pressure of 0.5 bar. The mixture was then stirred at a temperature between 18 and 23° C. by cooling the vessel jacket. A vacuum was applied to the vessel when no more hydrogen gas was consumed and when there was no further exotherm. Nitrogen gas was then charged into the vessel at 0.5 bar and a vacuum was reapplied, followed by a second charge of 0.5 bar nitrogen gas. When the HPLC of a filtered aliquot showed that none of the 7-[4-nitro-3-(trifluoromethyl) phenyl]-7-azabicyclo[2.2.1]heptane (19) remained (e.g., ≤0.5%), the reaction mixture was transferred to a receiving flask under nitrogen atmosphere via a filter funnel using a Celite filter. The Celite filter cake was washed with 2-methyltetrahydrofuran (3 L, 2 vol). The washings and filtrate were charged into a vessel equipped with stirring, temperature control, and a nitrogen atmosphere. 4M HCl in 1,4-dioxane (1 vol) was added continuously over 1 h into the vessel at 20° C. The mixture was stirred for an additional 10 h (or overnight), filtered, and washed with 2-methyltetrahydrofuran (2 vol) and dried to generate 1519 g of the hydrochloride salt of 4-(7-azabicyclo[2.2.1]heptan-7-yl)-2-(trifluoromethyl)aniline (20.HCl) as a white crystalline solid (approximately 97% yield).

Alternative Preparation of hydrochloride salt of 7-[4-amino-3-(trifluoromethyl)phenyl]-7-azabicyclo[2.2.1]heptane (20.HCl)

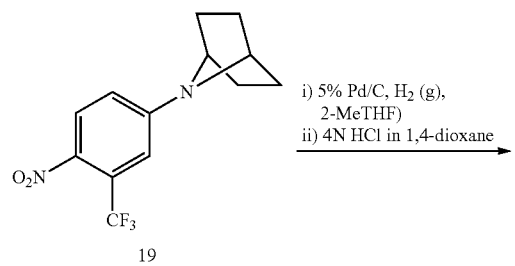

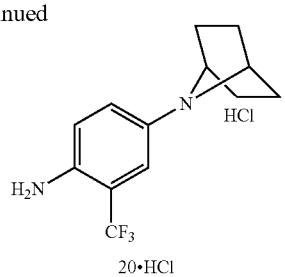

In a Büchi Hydrogenator (20 L capacity), palladium on carbon (5% w/w) (150 g) was introduced under nitrogen followed by the addition of 7-[4-nitro-3-(trifluoromethyl) phenyl]-7-azabicyclo[2.2.1]heptane 19 (1500 g) and 2-methyltetrahydrofuran (10.5 L, 7 vol). Hydrogen gas was charged into the vessel to a pressure of 0.5 bar. A vacuum was briefly applied (2 min), followed by the introduction of hydrogen gas to a pressure of 0.5 bar. This process was repeated 2 more times, and then hydrogen gas was charged to the hydrogenator continuously at 0.5 bar, and stirring was commenced. The temperature of the reaction mixture was maintained at 18 to 23° C. by cooling the vessel jacket. A vacuum was applied to the vessel when no more hydrogen gas was consumed and when there was no further exotherm. Nitrogen gas was then charged to the vessel, and a vacuum was re-applied, followed by a nitrogen gas charge at 0.5 bar. The reaction was deemed complete when an HPLC of a filtered aliquot showed that 7-[4-nitro-3-(trifluoromethyl)phenyl]-7-azabicyclo[2.2.1]heptane was not detected (≤0.5%). The reaction mixture was then filtered through Celite. The remaining slurry was transferred to a receiving flask under nitrogen gas via a filter funnel containing a Celite filter. The Celite cake was washed with 2-methyltetrahydrofuran (3 L, 2 vol). The filtrate and the washings were transferred to a vessel equipped with a stirring mechanism, temperature control, and a nitrogen atmosphere. 4M HCl in 1,4-dioxane (1 vol) was added continuously over 1 h to the vessel at 20° C. The resulting mixture was stirred for an additional 10 h, filtered and washed with 2-methyltetrahydrofuran (2 vol) and dried to generate 1519 g of 7-[4-amino-3-(trifluoromethyl)phenyl]-7-azabicyclo[2.2.1]heptane hydrochloride (20.HCl) as a white crystalline solid.

N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Form A-HCl)

2-Methyltetrahydrofuran (0.57 L, 1.0 vol) was charged into a 30 L jacketed reactor vessel, followed by the addition of the hydrochloride salt of 4-(7-azabicyclo[2.2.1]heptan-7-yl)-2-(trifluoromethyl)aniline (20.HCl) (791 g, 2.67 mol) and 4-oxo-5-(trifluoromethyl)-1,4-dihydroquinoline-3-carboxylic acid (17) (573 g, 2.23 mol) and an additional 5.2 L (9.0 vol) of 2-methyltetrahydrofuran. Stirring commenced, and T3P in 2-methyltetrahydrofuran (2.84 kg, 4.46 mol) was added to the reaction mixture over 15 min. Pyridine (534.0 g, 546.0 mL, 6.68 mol) was then added via an addition funnel dropwise over 30 min. The mixture was warmed to 45° C. over about 30 min and stirred for 12-15 h. HPLC analysis indicated that 4-oxo-5-(trifluoromethyl)-1,4-dihydroquinoline-3-carboxylic acid was present in an amount less than 2%. The mixture was then cooled to room temperature. 2-Methyltetrahydrofuran (4 vol, 2.29 L) was added followed by water (6.9 vol, 4 L), while the temperature was maintained below 30° C. The water layer was removed and the organic layer was carefully washed twice with NaHCO$_3$ saturated aqueous solution. The organic layer was then washed with 10% w/w citric acid (5 vol) and finally with water (7 vol). The mixture was polished filtered and transferred into another dry vessel. Seed crystals of N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Form A-HCl) (3.281 g, 5.570 mmol) from an earlier batch were added. HCl (g) (10 eq) was bubbled over 2 h and the mixture was stirred overnight. The resulting suspension was filtered, washed with 2-methyltetrahydrofuran (4 vol), suction dried and oven dried at 60° C. until constant weight generating 868 g of N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Form A-HCl).

Example Compound 3 Form B HCl Salt

N-(4-(7-azabicyclo[2.2.1]heptan-7-yl)-2-(trifluoromethyl)phenyl)-4-oxo-5-(trifluoromethyl)-1,4-dihydroquinoline-3-carboxamide hydrochloride (Form B-HCl)

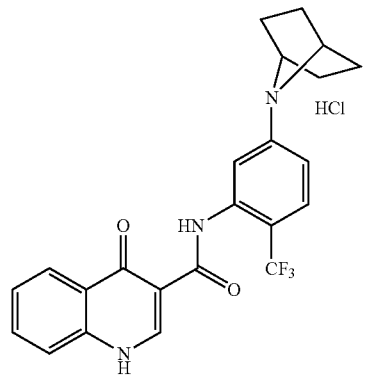

Example Compound 3
Form A Hydrochloride Salt
(Form A-HCl)

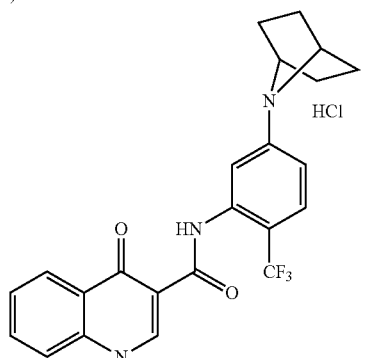

Example Compound 3
Form B Hydrochloride Salt
(Form B-HCl)

2-Methyltetrahydrofuran (100 mL) was charged into a 3-necked flask having a nitrogen atmosphere equipped with a stirrer. Example Compound 3 Form A-HCl (Example 3B, 55 g, 0.103 mol) was added to the flask, followed by 349 mL of 2-methyltetrahydrofuran, and stirring commenced. 28 mL of water was added into the flask and the flask was warmed to an internal temperature of 60° C. and stirred for 48 h. The flask was cooled to room temperature and stirred for 1 h. The reaction mixture was vacuum filtered until the filter cake was dry. The solid filter cake was washed with 2-methyltetrahydrofuran (4 vol) twice. The solid filter cake remained under vacuum suction for a period of about 30 minutes and was transferred to a drying tray. The filter cake was dried to a constant weight under vacuum at 60° C., to give Example Compound 3 Form B-HCl as a white crystalline solid (49 g) (approximately 90% yield).

Example Compound 6

Preparation of N-(4-(7-azabicyclo[2.2.1]heptan-7-yl)-2-cyanophenyl)-5-methyl-4-oxo-1,4-dihydroquinoline-3-carboxamide The preparation of the title compound is depicted in Scheme 11.

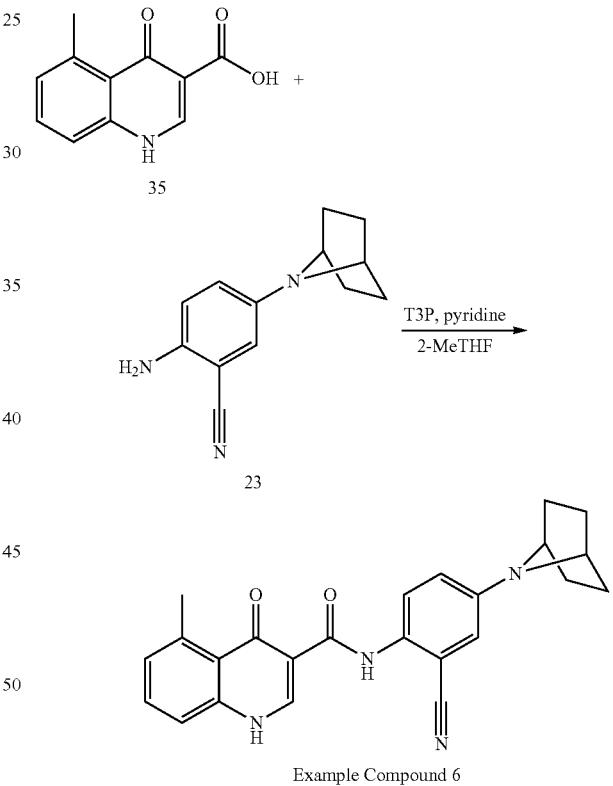

To a solution of 5-methyl-4-oxo-1,4-dihydroquinoline-3-carboxylic acid 35 (162 mg, 0.80 mmol) and 2-amino-5-(7-azabicyclo[2.2.1]heptan-7-yl)benzonitrile 23 (170 mg, 0.80 mmol) in 2-methyltetrahydrofuran (1.5 mL) was added propyl phosphonic acid cyclic anhydride (50% solution in ethyl acetate, 949.5 µL, 1.605 mmol) and pyridine (126 mg, 129 µL, 1.60 mmol). The reaction was capped and heated at 100° C. for 65 min with microwave irradiation. The reaction was cooled to room temperature, diluted with ethyl acetate (10 mL), and quenched with saturated Na$_2$CO$_3$ solution (6 mL). The organic layer was dried over Na$_2$SO$_4$, filtered and concentrated. Purification by silica gel chromatography (0-35% ethyl acetate in dichloromethane) provided N-(4-(7-azabicyclo[2.2.1]heptan-7-yl)-2-cyanophenyl)-5-methyl-4-oxo-1,4-dihydroquinoline-3-carboxamide (157 mg, 49% yield). LC/MS m/z 399.3 [M+H]$^+$, retention time 1.47 min (RP-C$_{18}$, 10-99% CH$_3$CN/0.05% TFA over 3 min). $^1$H NMR (400.0 MHz, DMSO-d$_6$) δ 12.77 (s, 1H), 12.75 (s, 1H), 8.77 (s, 1H), 8.11 (d, J=9.1 Hz, 1H), 7.64-7.60 (m, 1H), 7.55 (d, J=8.0 Hz, 1H), 7.34 (d, J=2.8 Hz, 1H), 7.27 (dd, J=2.8, 9.1 Hz, 1H), 7.23 (d, J=7.2 Hz, 1H), 4.32 (s, 2H), 2.91 (s, 3H), 1.65 (d, J=7.2 Hz, 4H), 1.42 (d, J=6.8 Hz, 4H).

Example Compound 13

N-[4-(7-azabicyclo[2.2.1]heptan-7-yl)-2-(3-dimethylaminoprop-1-ynyl)phenyl]-4-oxo-5-(trifluoromethyl)-1H-quinoline-3-carboxamide The preparation of the title compound is depicted in Scheme 12.

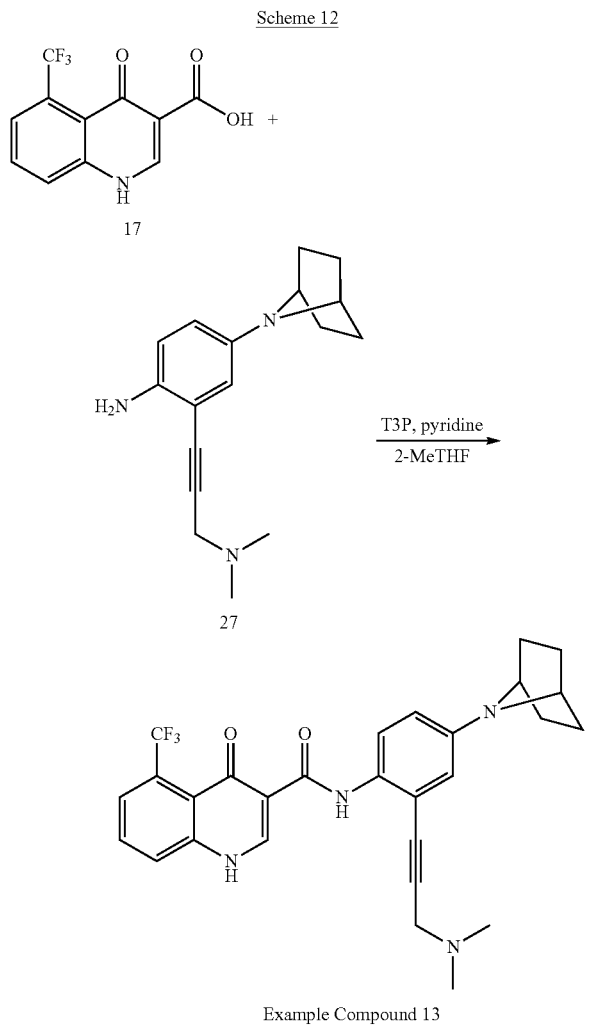 [SMILES: O=C(O)c1c[nH]c2cccc(C(F)(F)F)c2c1=O ; CN(C)CC#Cc1cc(N2C3CCC2CC3)ccc1N ; CN(C)CC#Cc1cc(N2C3CCC2CC3)ccc1NC(=O)c1c[nH]c2cccc(C(F)(F)F)c2c1=O]

Example Compound 13

To a solution of 4-oxo-5-(trifluoromethyl)-1H-quinoline-3-carboxylic acid 17 (19 mg, 0.07 mmol) and 4-(7-azabicyclo[2.2.1]heptan-7-yl)-2-(3-dimethylaminoprop-1-ynyl)aniline 27 (20 mg, 0.07 mmol) in 2-methyltetrahydrofuran (190.9 μL) was added T3P (118 mg, 0.19 mmol) and pyridine (12 mg, 12 μL, 0.15 mmol). The reaction was heated at 100° C. for 30 min under microwave irradiation. The reaction was diluted with EtOAc and quenched with saturated aqueous NaHCO$_3$ (50 mL). The layers were separated, and the aqueous layer was extracted twice with EtOAc. The combined organics were washed once with water, dried over Na$_2$SO$_4$, filtered and concentrated. The residue was purified by reverse phase HPLC (0-99% CH$_3$CN/0.05% TFA) to give N-[4-(7-azabicyclo[2.2.1]heptan-7-yl)-2-(3-dimethylaminoprop-1-ynyl)phenyl]-4-oxo-5-(trifluoromethyl)-1H-quinoline-3-carboxamide (8 mg, 17% yield). LC/MS m/z 509.7 [M+H]$^+$, retention time 1.06 min (RP-C$_{18}$, 10-99% CH$_3$CN/0.05% TFA over 3 min). $^1$H NMR (400.0 MHz, DMSO-d$_6$) δ 13.23 (d, J=6.8 Hz, 1H), 12.40 (s, 1H), 10.31 (s, 1H), 8.96 (d, J=6.6 Hz, 1H), 8.40 (d, J=9.0 Hz, 1H), 8.08-8.06 (m, H), 8.07 (dd, J=1.5 Hz, 8.1 Hz, 1H), 8.00-7.95 (m, 2H), 7.15-7.09 (m, 2H), 4.49 (s, 2H), 4.29 (s, 2H), 2.94 (s, 6H), 1.67 (d, J=7.2 Hz, 4H), 1.44 (d, J=7.0 Hz, 4H).

Example Compound 5

Endo-N-[4-[(5S)-5-[tert-butyl(dimethyl)silyl]oxy-7-azabicyclo[2.2.1]heptan-7-yl]-2-(trifluoromethyl)phenyl]-4-oxo-5-(trifluoromethyl)-1H-quinoline-3-carboxamide The preparation of the title compound is depicted in Scheme 13.

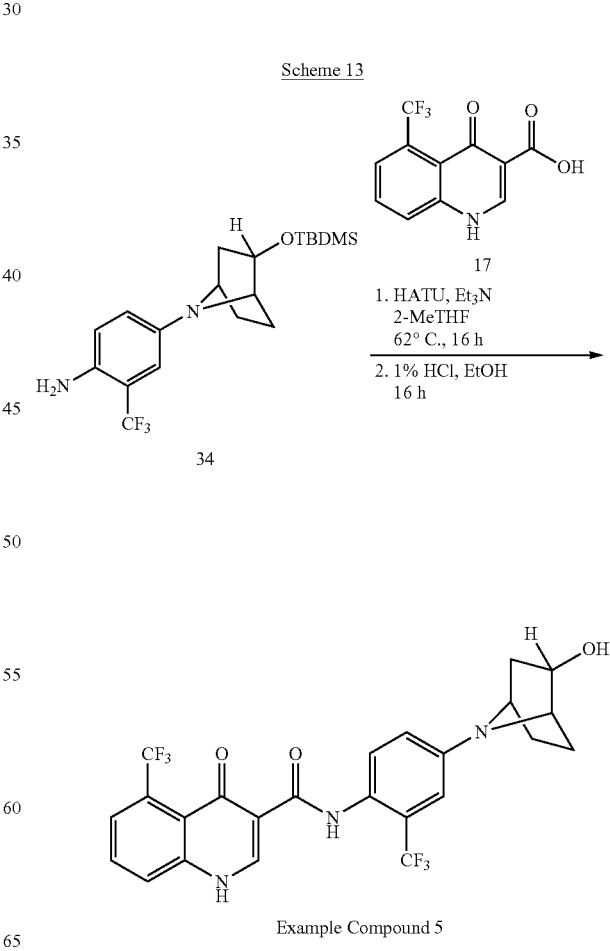

Example Compound 5

Preparation of endo-N-[4-[(5S)-5-[tert-butyl(dimethyl)silyl]oxy-7-azabicyclo[2.2.1]heptan-7-yl]-2-(trifluoromethyl)phenyl]-4-oxo-5-(trifluoromethyl)-1H-quinoline-3-carboxamide To a solution of 4-oxo-5-(trifluoromethyl)-1H-quinoline-3-carboxylic acid 17 (148 mg, 0.58 mmol), O-(7-Azabenzotriazol-1-yl)-N,N,N',N'-tetramethyluronium hexafluorophosphate (HATU) (306 mg, 0.81 mmol) in 2-methyltetrahydrofuran (2.2 mL) was added endo-4-[5-[tert-butyl(dimethyl)silyl]oxy-7-azabicyclo[2.2.1]heptan-7-yl]-2-(trifluoromethyl)aniline 34 (222 mg, 0.58 mmol) followed by triethylamine (146 mg, 201 μL, 1.44 mmol). The reaction mixture was heated at 62° C. for 16 h. The reaction mixture was allowed to cool to room temperature, and partitioned between 2-methyltetrahydrofuran/water, separated and the aqueous layer was extracted once more with 2-methyltetrahydrofuran, the organic layers were combined, dried over $Na_2SO_4$, filtered and concentrated to dryness. Purification by silica gel chromatography (0-30% ethyl acetate in dichloromethane) afforded endo-N-[4-[(5S)-5-[tert-butyl(dimethyl)silyl]oxy-7-azabicyclo[2.2.1]heptan-7-yl]-2-(trifluoromethyl)phenyl]-4-oxo-5-(trifluoromethyl)-1H-quinoline-3-carboxamide (285 mg, 79% yield). $^1$H NMR (400.0 MHz, DMSO-$d_6$) δ 13.07 (s, 1H), 12.16 (s, 1H), 8.88 (s, 1H), 8.04 (dd, J=2.2, 7.3 Hz, 1H), 7.95-7.89 (m, 3H), 7.22 (dd, J=2.4, 8.9 Hz, 1H), 7.16 (d, J=2.6 Hz, 1H), 4.29 (m, 3H), 2.16-2.07 (m, 2H), 1.62-1.43 (m, 3H), 1.05-1.01 (m, 1H), 0.89 (s, 9H), 0.08 (d, J=1.4 Hz, 6H).

Preparation of endo-N-[4-[(5S)-5-hydroxy-7-azabicyclo[2.2.1]heptan-7-yl]-2-(trifluoromethyl)phenyl]-4-oxo-5-(trifluoromethyl)-1H-quinoline-3-carboxamide Endo-N-[4-[(5S)-5-[tert-butyl(dimethyl)silyl]oxy-7-azabicyclo[2.2.1]heptan-7-yl]-2-(trifluoromethyl)phenyl]-4-oxo-5-(trifluoromethyl)-1H-quinoline-3-carboxamide (281 mg, 0.45 mmol) was dissolved in 1% HCl/Ethanol (2 mL of 1% w/w) solution and allowed to stir a room temperature for 16 h, resulting in a white precipitate. The reaction was diluted with diethyl ether and filtered. The collected solid was dissolved in ethyl acetate/saturated aqueous $NaHCO_3$ solution. The layers were separated and the aqueous layer was extracted once more with ethyl acetate. The organic layers were washed twice with water, dried over $Na_2SO_4$, filtered and concentrated to dryness to yield endo-N-[4-[(5S)-5-hydroxy-7-azabicyclo[2.2.1]heptan-7-yl]-2-(trifluoromethyl)phenyl]-4-oxo-5-(trifluoromethyl)-1H-quinoline-3-carboxamide (190 mg, 83%). $^1$H NMR (400.0 MHz, DMSO-$d_6$) δ 13.07 (s, 1H), 12.15 (s, 1H), 8.88 (s, 1H), 8.04 (dd, J=2.2, 7.4 Hz, 1H), 7.95-7.88 (m, 3H), 7.19 (dd, J=2.4, 9.0 Hz, 1H), 7.12 (d, J=2.6 Hz, 1H), 5.00 (d, J=4.2 Hz, 1H), 4.25-4.13 (m, 1H), 4.21-4.19 (m, 1H), 4.16-4.13 (m, 1H), 2.15-2.08 (m, 2H), 1.61-1.55 (m, 1H), 1.47-1.44 (m, 2H) and 1.03 (dd, J=3.4, 12.3 Hz, 1H).

Analytical data for the compounds of Table 1 is shown below:

TABLE 2

| Example Compound No. | LC/MS M + 1 | LC/RT$^a$ minutes | NMR |
|---|---|---|---|
| 1 | 456.50 | 1.76 | $^1$H NMR (400.0 MHz, DMSO-$d_6$) δ 12.94 (d, J = 6.1 Hz, 1H), 12.36 (s, 1H), 8.80 (d, J = 6.8 Hz, 1H), 8.13 (s, 1H), 7.98 (d, J = 8.9 Hz, 1H), 7.68-7.63 (m, 2H), 7.10 (d, J = 8.5 Hz, 1H), 7.01 (s, 1H), 4.28 (s, 2H), 2.48 (s, 3H), 2.02-2.00 (m, 2H), 1.86-1.77 (m, 5H), 1.45-1.42 (m, 1H), 1.31 (d, J = 11.1 Hz, 2H). |
| 2 | 458.20 | 1.20 | $^1$H NMR (400.0 MHz, DMSO-$d_6$) δ 12.89 (s, 1H), 12.43 (s, 1H), 8.79 (s, 1H), 8.00 (d, J = 8.9 Hz, 1H), 7.72-7.68 (m, 2H), 7.44 (dd, J = 2.9, 9.0 Hz, 1H), 7.22 (dd, J = 2.5, 9.0 Hz, 1H), 7.15 (d, J = 2.6 Hz, 1H), 4.33 (s, 2H), 3.91 (s, 3H), 1.67 (d, J = 6.9 Hz, 4H), 1.43 (d, J = 6.9 Hz, 4H). |
| 3 | 496.0 | 1.48 | $^1$H NMR (400.0 MHz, DMSO-$d_6$) δ 13.08 (s, 1H), 12.16 (s, 1H), 8.88 (s, 1H), 8.04 (dd, J = 2.1, 7.4 Hz, 1H), 7.95-7.88 (m, 3H), 7.22 (dd, 2.5, 8.9 Hz, 1H), 7.16 (d, J = 2.5 Hz, 1H), 4.33 (s, 2H), 1.67 (d, J = 6.9 Hz, 4H), 1.44 (d, J = 6.9 Hz, 4H). |
| 4 | 458.50 | 1.22 | $^1$H NMR (400.0 MHz, DMSO-$d_6$) δ 13.12 (d, J = 6.7 Hz, 1H), 12.50 (s, 1H), 8.78 (d, J = 6.8 Hz, 1H), 8.10 (d, J = 9.1 Hz, 1H), 7.78-7.72 (m, 3H), 7.65 (d, J = 7.7 Hz, 1H), 7.39 (d, J = 7.3 Hz, 1H), 7.33 (s, 1H), 5.20 (s, 2H), 4.47 (s, 2H), 1.74 (d, J = 6.7 Hz, 4H), 1.51 (d, J = 7.1 Hz, 4H). |
| 5 | 512.50 | 1.55 | $^1$H NMR (400.0 MHz, DMSO-$d_6$) δ 13.07 (s, 1H), 12.15 (s, 1H), 8.88 (s, 1H), 8.04 (dd, J = 2.2, 7.4 Hz, 1H), 7.95-7.88 (m, 3H), 7.19 (dd, J = 2.4, 9.0 Hz, 1H), 7.12 (d, J = 2.6 Hz, 1H), 5.00 (d, J = 4.2 Hz, 1H), 4.25-4.13 (m, 1H), 4.21-4.19 (m, 1H), 4.16-4.13 (m, 1H), 2.15-2.08 (m, 2H), 1.61-1.55 (m, 1H), 1.47-1.44 (m, 2H) and 1.03 (dd, J = 3.4, 12.3 Hz, 1H). |
| 6 | 399.30 | 1.47 | $^1$H NMR (400.0 MHz, DMSO-$d_6$) δ 12.77 (s, 1H), 12.75 (s, 1H), 8.77 (s, 1H), 8.11 (d, J = 9.1 Hz, 1H), 7.64-7.60 (m, 1H), 7.55 (d, J = 8.0 Hz, 1H), 7.34 (d, J = 2.8 Hz, 1H), 7.27 (dd, J = 2.8, 9.1 Hz, 1H), 7.23 (d, J = 7.2 Hz, 1H), 4.32 (s, 2H), 2.91 (s, 3H), 1.65 (d, J = 7.2 Hz, 4H), 1.42 (d, J = 6.8 Hz, 4H). |

TABLE 2-continued

| Example Compound No. | LC/MS M + 1 | LC/RT$^a$ minutes | NMR |
|---|---|---|---|
| 7 | 453.0 | 1.62 | $^1$H NMR (400.0 MHz, DMSO-d$_6$) δ 13.28 (d, J = 6.4 Hz, 1H), 12.07 (s, 1H), 8.95 (d, J = 6.5 Hz, 1H), 8.69 (s, 1H), 8.16 (dd, J = 1.5, 8.7 Hz, 1H), 8.01 (d, J = 8.8 Hz, 1H), 7.91 (d, J = 8.7 Hz, 1H), 7.28 (d, J = 7.8 Hz, 1H), 7.22 (s, 1H), 4.38 (s, 2H), 1.69 (d, J = 6.4 Hz, 4H), 1.46 (d, J = 6.9 Hz, 4H). |
| 8 | 512.10 | 1.35 | $^1$H NMR (400.0 MHz, DMSO-d$_6$) δ 13.07 (s, 1H), 12.13 (s, 1H), 8.88 (s, 1H), 8.05-8.02 (m, 1H), 7.95-7.86 (m, 3H), 7.18 (d, J = 9.0 Hz, 1H), 7.12 (d, J = 2.5 Hz, 1H), 4.74 (d, J = 5.2 Hz, 1H), 4.33 (m, 1H), 4.11 (m, 1H), 3.77 (m, 1H), 1.82 (dd, J = 7.3, 12.5 Hz, 1H), 1.56-1.48 (m, 3H), 1.25 (m, 2H). |
| 9 | 442.10 | 1.20 | $^1$H NMR (400.0 MHz, DMSO-d$_6$) δ 12.84 (s, 1H), 12.43 (s, 1H), 8.81 (s, 1H), 8.12 (s, 1H), 8.00 (d, J = 8.9 Hz, 1H), 7.64 (m, 2H), 7.21 (dd, J = 2.5, 9.0 Hz, 1H), 7.15 (d, J = 2.6 Hz, 1H), 4.32 (s, 2H), 2.47 (s, 3H), 1.67 (d, J = 7.4 Hz, 4H), 1.43 (d, J = 6.9 Hz, 4H). |
| 10 | 442.10 | 1.40 | $^1$H NMR (400.0 MHz, DMSO-d$_6$) δ 12.68 (s, 1H), 12.41 (s, 1H), 8.75 (s, 1H), 7.94 (d, J = 8.9 Hz, 1H), 7.63-7.60 (m, 1H), 7.54 (d, J = 7.8 Hz, 1H), 7.23-7.20 (m, 2H), 7.15 (d, J = 2.7 Hz, 1H), 4.33 (s, 2H), 2.89 (s, 3H), 1.67 (d, J = 6.7 Hz, 4H), 1.44 (d, J = 6.9 Hz, 4H). |
| 11 | 444.0 | 1.30 | $^1$H NMR (400.0 MHz, DMSO-d$_6$) δ 13.55 (s, 1H), 13.31 (d, J = 7.2 Hz, 1H), 11.58 (s, 1H), 8.86 (d, J = 6.9 Hz, 1H), 8.01 (d, J = 9.0 Hz, 1H), 7.66 (t, J = 8.2 Hz, 1H), 7.29 (d, J = 8.8 Hz, 1H), 7.23 (s, 1H), 7.17 (d, J = 7.7 Hz, 1H), 6.80 (d, J = 7.5 Hz, 1H), 4.39 (s, 2H), 1.69 (d, J = 7.3 Hz, 4H), 1.46 (d, J = 7.0 Hz, 4H). |
| 12 | 510.5 | 1.95 | $^1$H NMR (400.0 MHz, DMSO-d$_6$) δ 13.16 (d, J = 5.7 Hz, 1H), 12.07 (s, 1H), 8.87 (d, J = 6.6 Hz, 1H), 8.05 (dd, J = 2.1, 7.3 Hz, 1H), 7.96-7.92 (m, 2H), 7.87 (d, J = 9.0 Hz, 1H), 7.09 (d, J = 9.1 Hz, 1H), 7.00 (s, 1H), 4.28 (s, 2H), 2.02-2.00 (m, 2H), 1.88-1.73 (m, 5H), 1.45-1.42 (m, 1H), 1.31 (d, J = 11.6 Hz, 2H). |
| 13 | 509.7 | 1.06 | $^1$H NMR (400.0 MHz, DMSO-d$_6$) δ 13.23 (d, J = 6.8 Hz, 1H), 12.40 (s, 1H), 10.31 (s, 1H), 8.96 (d, J = 6.6 Hz, 1H), 8.40 (d, J = 9.0 Hz, 1H), 8.08-8.06 (m, H), 8.07 (dd, J = 1.5 Hz, 8.1 Hz, 1H), 8.00-7.95 (m, 2H), 7.15-7.09 (m, 2H), 4.49 (s, 2H), 4.29 (s, 2H), 2.94 (s, 6H), 1.67 (d, J = 7.2 Hz, 4H), 1.44 (d, J = 7.0 Hz, 4H). |
| 14 | 455.7 | 1.04 | $^1$H NMR (400.0 MHz, DMSO-d$_6$) δ 12.63 (s, 2H), 8.75 (s, 1H), 8.38 (d, J = 8.8 Hz, 1H), 7.62-7.58 (m, 1H), 7.52 (d, J = 8.1 Hz, 1H), 7.21 (d, J = 7.2 Hz, 1H), 6.96-6.93 (m, 2H), 4.24 (s, 2H), 3.70 (s, 2H), 2.92 (s, 3H), 2.28 (s, 6H), 1.65 (d, J = 7.0 Hz, 4H), 1.39 (d, J = 6.8 Hz, 4H). |

$^a$Retention Time

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl$^-$ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours. Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$, 10 glucose, 10 HEPES (pH adjusted to 7.35 with NaOH).

Identification of Potentiator Compounds

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$, 10 EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PICA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters. Examples of activities and efficacies of the compounds of Formula (I) are shown below in Table 3. The compound activity is illustrated with "+++" if activity was measured to be less than 2.0 µM, "++" if activity was measured to be from 2 µM to 5.0 µM, "+" if activity was measured to be greater than 5.0 µM, and "−" if no data was available. The efficacy is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with 4-methyl-2-(5-phenyl-1H-pyrazol-3-yl)phenol.

TABLE 3

| Example Compound No. | Activity EC$_{50}$ (µm) | % Efficacy |
|---|---|---|
| 1 | +++ | ++ |
| 2 | +++ | ++ |
| 3 | +++ | ++ |
| 4 | +++ | ++ |
| 5 | +++ | +++ |
| 6 | +++ | +++ |
| 7 | +++ | ++ |
| 8 | +++ | ++ |
| 9 | +++ | ++ |
| 10 | +++ | +++ |
| 11 | +++ | ++ |
| 12 | +++ | ++ |
| 13 | +++ | ++ |
| 14 | +++ | ++ |

What is claimed is:

1. A compound of Formula (I):

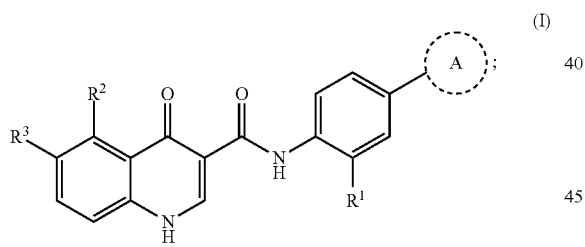

(I)

or pharmaceutically acceptable salts thereof, wherein:
ring A is selected from:

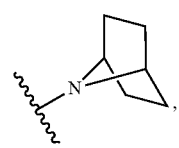

(a)

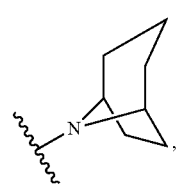

(b)

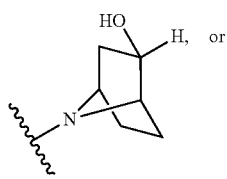

(c)

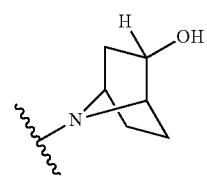

(d)

wherein:
R$^1$ is —CF$_3$, —CN, or —C≡CCH$_2$N(CH$_3$)$_2$;
R$^2$ is hydrogen, —CH$_3$, —CF$_3$, —OH, or —CH$_2$OH;
R$^3$ is hydrogen, —CH$_3$, —OCH$_3$, or —CN;
provided that both R$^2$ and R$^3$ are not simultaneously hydrogen.

2. The compound according to claim 1, wherein ring A is

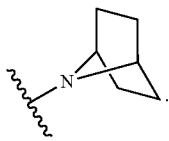

(a)

3. The compound according to claim 1, wherein ring A is

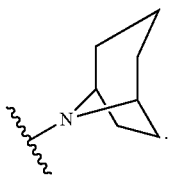

(b)

4. The compound according to claim 1, wherein ring A is (c)

5. The compound according to claim 1, wherein ring A is

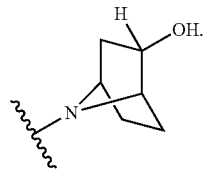 (d)

6. The compound according to claim 1, wherein R¹ is —CF₃.

7. The compound according to claim 1, wherein R¹ is —CN.

8. The compound according to claim 1, wherein R¹ is —C≡CCH₂N(CH₃)₂.

9. The compound according to any one of claims 6-8, wherein R² is hydrogen.

10. The compound according to any one of claims 6-8, wherein R² is —CH₃.

11. The compound according to any one of claims 6-8, wherein R² is —CF₃.

12. The compound according to any one of claims 6-8, R² is —OH.

13. The compound according to any one of claims 6-8, wherein R² is —CH₂OH.

14. The compound according to claim 9, wherein R³ is —CH₃.

15. The compound according to claim 9, wherein R³ is —OCH₃.

16. The compound according to claim 9, wherein R³ is —CN.

17. A compound selected from

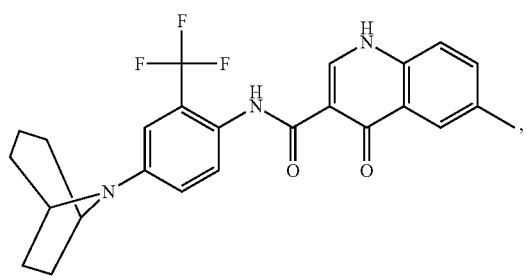

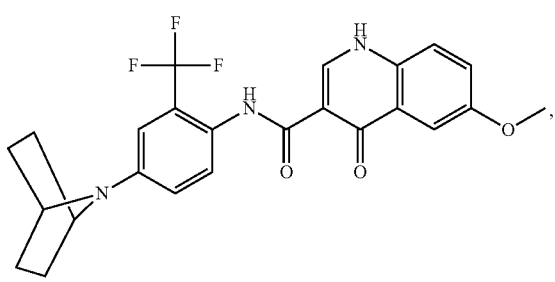

-continued

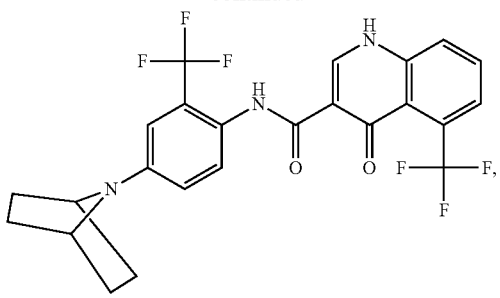

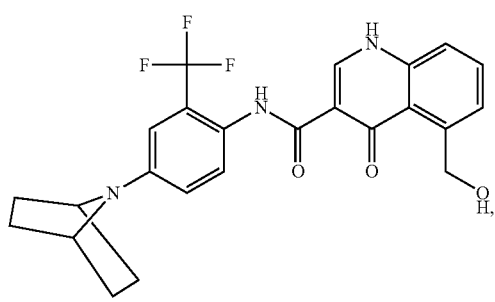

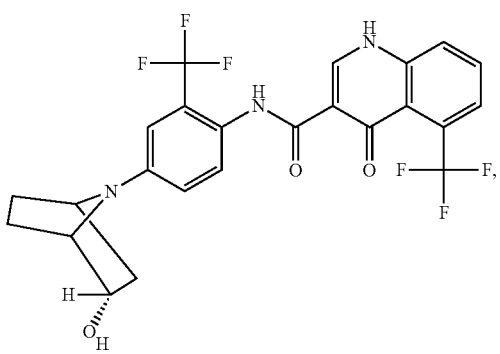

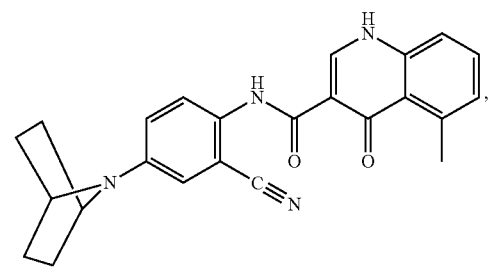

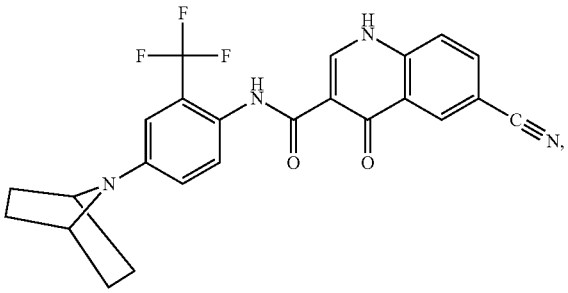

-continued

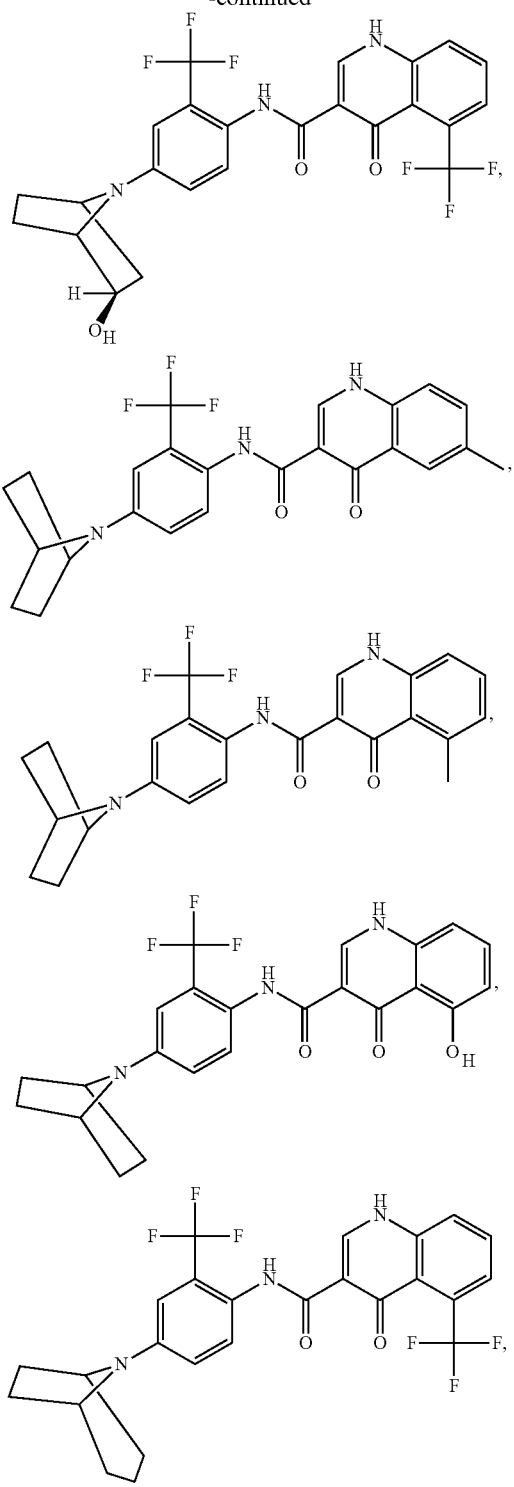

-continued

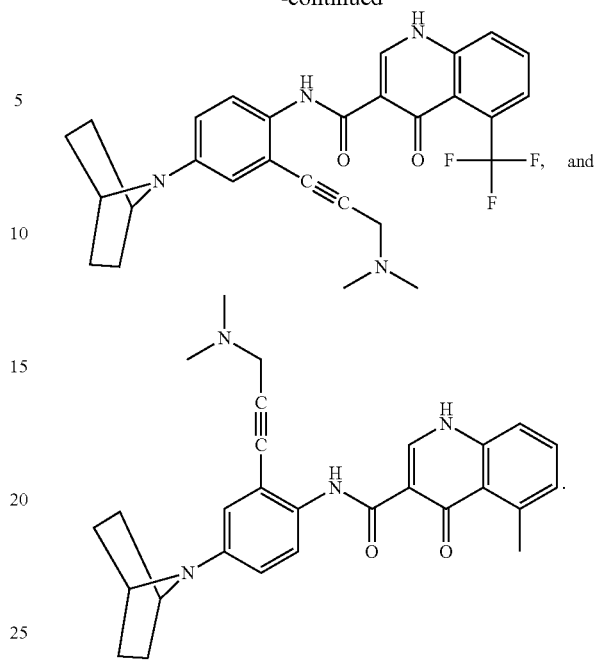

18. A pharmaceutical composition comprising a compound according to claim 1 and a pharmaceutically acceptable carrier or adjuvant.

19. The pharmaceutical composition according to claim 18, further comprising an additional agent selected from a mucolytic agent, a bronchodialator, an antibiotic, an anti-infective agent, an anti-inflammatory agent, a CFTR modulator other than a compound of Formula (I), or a nutritional agent.

20. The pharmaceutical composition according to claim 19, wherein said additional agent is a CFTR modulator other than a compound of Formula (I).

21. A kit for use in measuring the activity of CFTR or a fragment thereof in a biological sample in vitro or in vivo, comprising:
   (i) a composition comprising a compound of Formula (I) according to claim 1;
   (ii) instructions for:
      a) contacting the composition with the biological sample;
      b) measuring activity of said CFTR or a fragment thereof.

22. The kit of claim 21, further comprising instructions for:
   a) contacting an additional composition with the biological sample;
   b) measuring the activity of said CFTR or a fragment thereof in the presence of said additional compound, and
   c) comparing the activity of the CFTR in the presence of the additional compound with the density of CFTR in the presence of a composition of Formula (I).

* * * * *